US011439425B2

United States Patent
Takayama et al.

(10) Patent No.: US 11,439,425 B2
(45) Date of Patent: Sep. 13, 2022

(54) SURGICAL PROCEDURE OF KNEE JOINT

(71) Applicant: OLYMPUS CORPORATION, Hachioji (JP)

(72) Inventors: Michio Takayama, Tokyo (JP); Takamitsu Sakamoto, Hachioji (JP); Ken Fujisaki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 249 days.

(21) Appl. No.: 16/686,664

(22) Filed: Nov. 18, 2019

(65) Prior Publication Data
US 2020/0078041 A1 Mar. 12, 2020

Related U.S. Application Data

(62) Division of application No. 15/337,596, filed on Oct. 28, 2016, now abandoned.

(51) Int. Cl.
*A61B 17/32* (2006.01)
*A61B 17/16* (2006.01)
*A61B 17/56* (2006.01)

(52) U.S. Cl.
CPC .. *A61B 17/320068* (2013.01); *A61B 17/1675* (2013.01); *A61B 2017/320004* (2013.01); *A61B 2017/32007* (2017.08); *A61B 2017/320072* (2013.01); *A61B 2017/320073* (2017.08); *A61B 2017/564* (2013.01)

(58) Field of Classification Search
CPC ........ A61B 17/320068; A61B 17/1675; A61B 17/1677
See application file for complete search history.

(56) References Cited

U.S. PATENT DOCUMENTS

| | | |
|---|---|---|
| 5,067,962 A | 11/1991 | Campbell et al. |
| 6,544,260 B1 | 4/2003 | Markel et al. |
| 8,709,089 B2 | 4/2014 | Lang et al. |
| 2004/0068267 A1 | 4/2004 | Harvie et al. |
| 2005/0054954 A1 | 3/2005 | Lidgren et al. |
| 2006/0030871 A1 | 2/2006 | Hain et al. |

(Continued)

FOREIGN PATENT DOCUMENTS

| | | |
|---|---|---|
| JP | H05-168642 A | 7/1993 |
| JP | 2006-334268 A | 12/2006 |

OTHER PUBLICATIONS

U.S. Appl. No. 14/878,571, filed Oct. 8, 2015 in the name of Sohei Ueda, et al.

(Continued)

*Primary Examiner* — Olivia C Chang
(74) *Attorney, Agent, or Firm* — Oliff PLC

(57) ABSTRACT

A surgical procedure of preparing bone holes to dispose an implanted tendon to a femur when performing reconstruction of a ligament in a knee joint, includes: forming a first bone hole in the femur; and applying ultrasonic vibration from a treatment portion of an ultrasonic treatment instrument to the femur, thereby cutting and expanding the first bone hole from the inside of the knee joint to the first bone hole of the femur along a predetermined depth, and forming a second bone hole having a polygonal shape, an approximately polygonal shape, an elliptical shape or an approximately elliptical shape to receive the implanted tendon.

16 Claims, 18 Drawing Sheets

(56) References Cited

U.S. PATENT DOCUMENTS

| | | | |
|---|---|---|---|
| 2006/0253050 A1* | 11/2006 | Yoshimine | A61H 23/0245 601/2 |
| 2009/0018654 A1* | 1/2009 | Schmieding | A61B 17/1675 623/13.14 |
| 2010/0121197 A1 | 5/2010 | Ota et al. | |
| 2010/0174368 A1 | 7/2010 | Lynch et al. | |
| 2010/0191173 A1 | 7/2010 | Kimura et al. | |
| 2010/0298894 A1 | 11/2010 | Bojarski et al. | |
| 2010/0312350 A1 | 12/2010 | Bonutti | |
| 2011/0196401 A1 | 8/2011 | Robertson et al. | |
| 2012/0165843 A1 | 6/2012 | Gannoe et al. | |
| 2013/0006278 A1 | 1/2013 | Mayer et al. | |
| 2013/0096471 A1 | 4/2013 | Slayton et al. | |
| 2014/0230995 A1 | 8/2014 | Schlottig et al. | |
| 2015/0165243 A1 | 6/2015 | Slayton et al. | |
| 2016/0338782 A1 | 11/2016 | Bowling et al. | |

OTHER PUBLICATIONS

U.S. Appl. No. 14/878,664, filed Oct. 8, 2015 in the name of Sohei Ueda, et al.
U.S. Appl. No. 14/878,684, filed Oct. 8, 2015 in the name of Sohei Ueda, et al.
Nov. 9, 2017 Office Action Issued in U.S. Appl. No. 14/878,684.
Nov. 28, 2017 Office Action Issued In U.S. Appl. No. 14/878,664.
Dec. 28, 2017 Office Action issued in U.S. Appl. No. 15/337,271.
U.S. Appl. No. 15/337,596, filed Oct. 28, 2016 in the name of Michio Takayama et al.
U.S. Appl. No. 15/337,271, filed Oct. 28, 2016 in the name of Sohei Ueda et al.
Jun. 5, 2018 Office Action Issued in U.S. Appl. No. 15/337,271.
Nov. 20, 2018 Office Action issued in U.S. Appl. No. 15/337,271.
Mar. 29, 2019 Office Action issued in U.S. Appl. No. 15/377,596.
Aug. 19, 2019 Office Action Issued in U.S. Appl. No. 15/337,596.

* cited by examiner

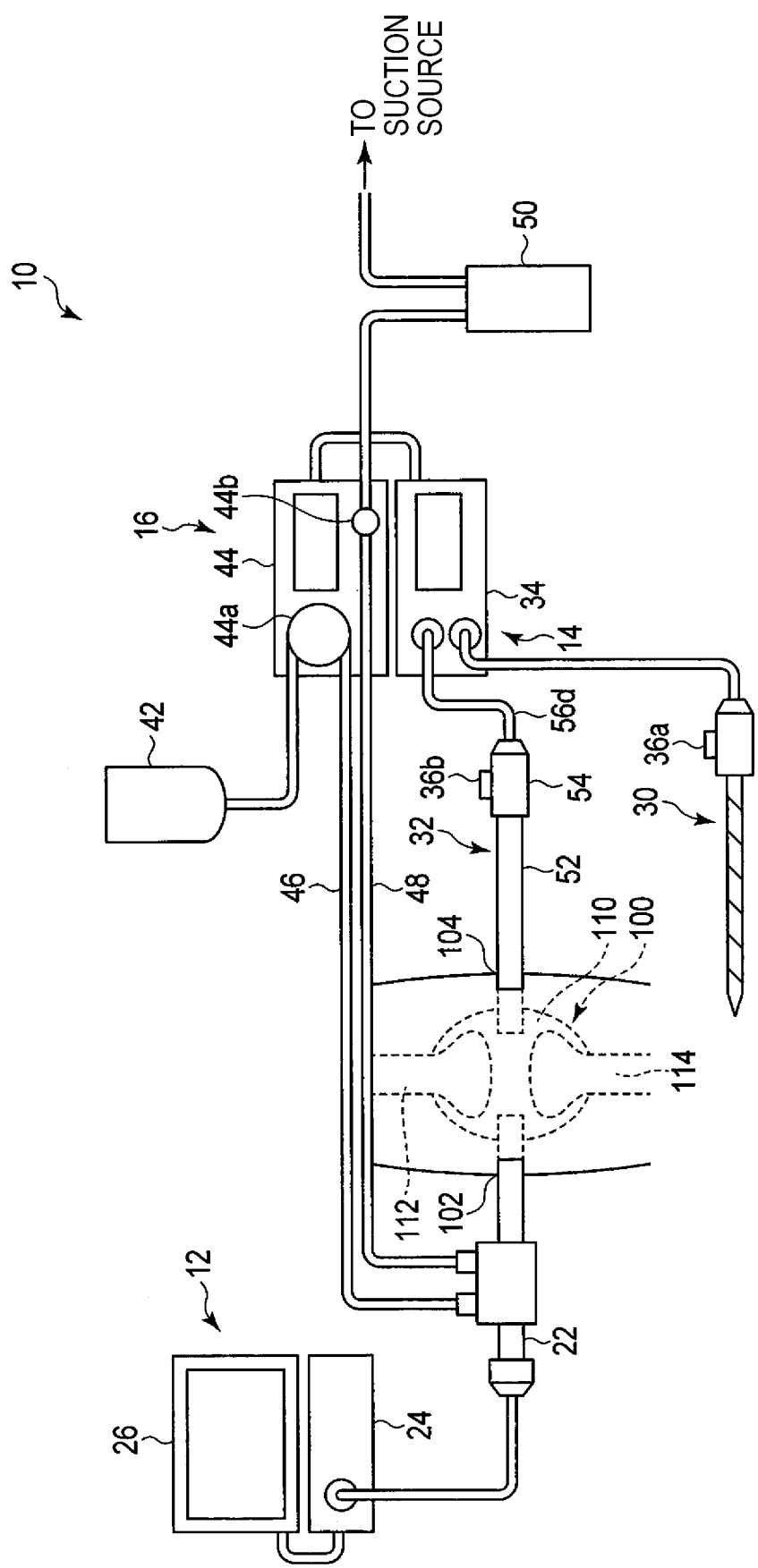
F I G. 1

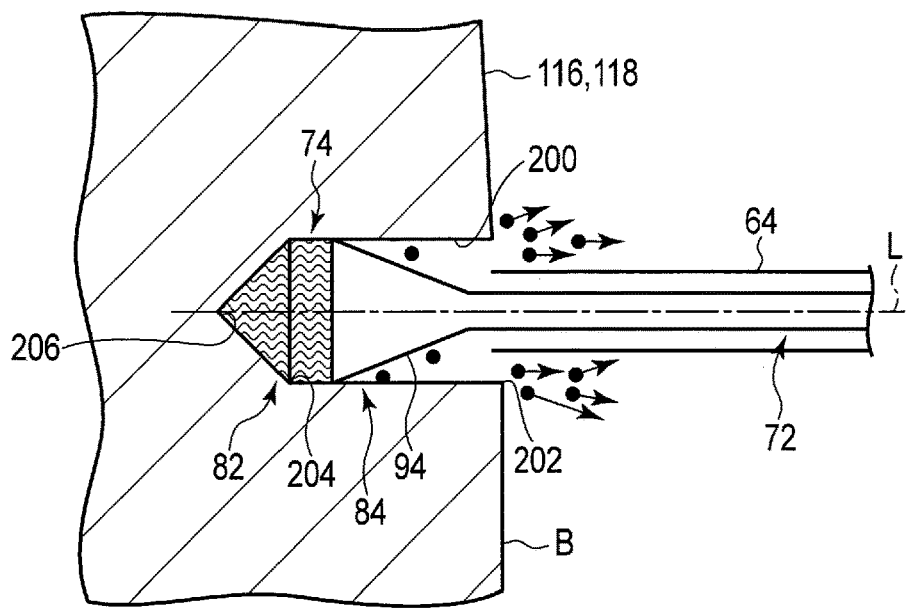
F I G. 4A
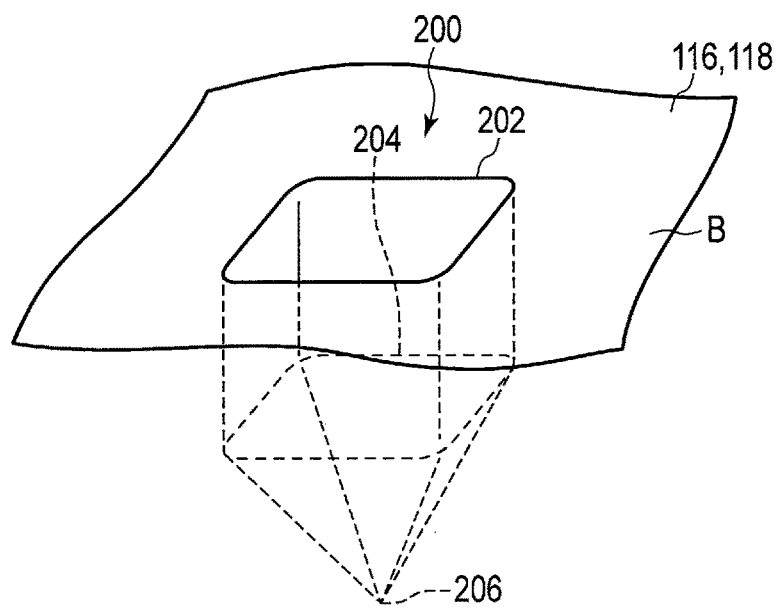
F I G. 4B

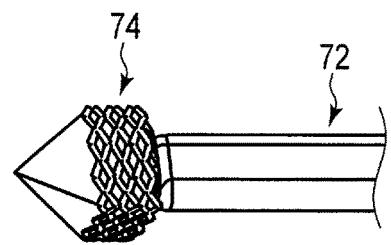
F I G. 5A
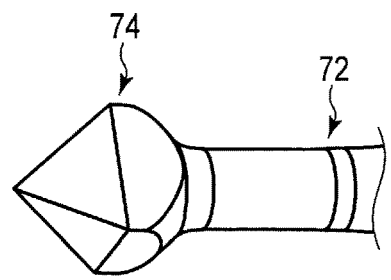
F I G. 5B
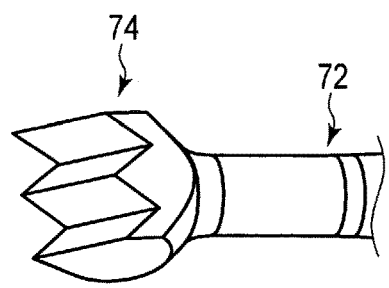
F I G. 6A
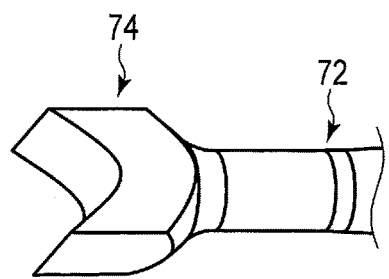
F I G. 6B
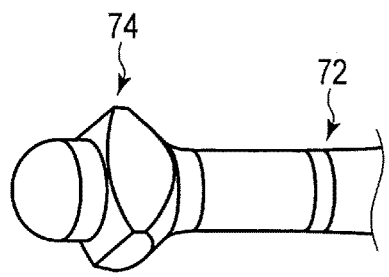
F I G. 6C

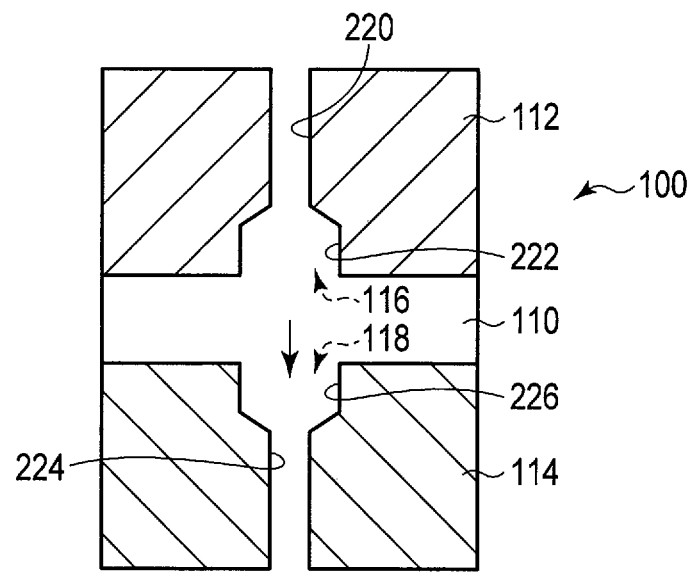
F I G. 8D
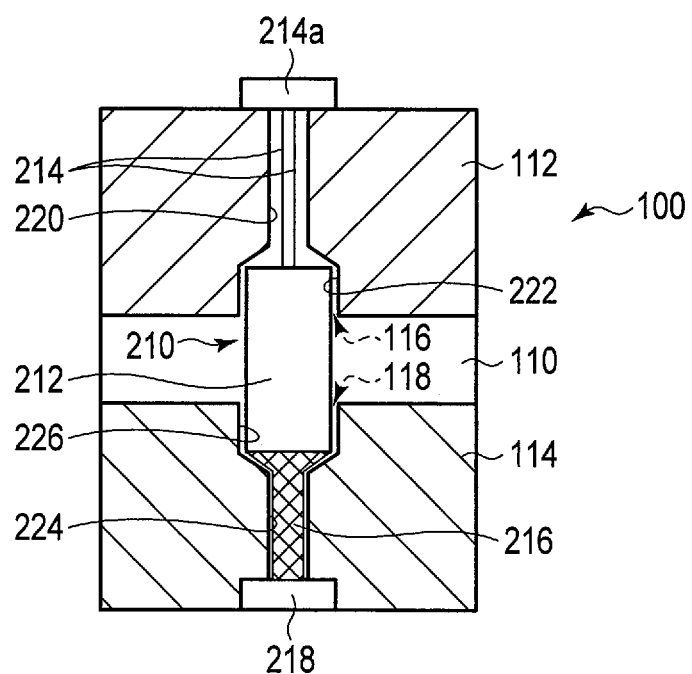
F I G. 8E

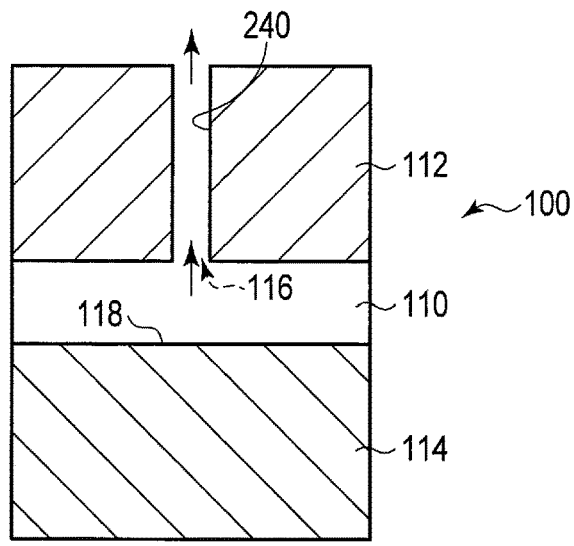
F I G. 10A
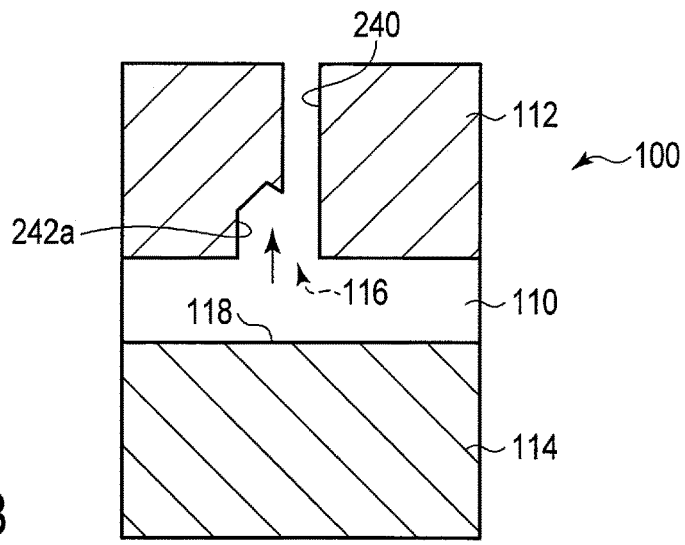
F I G. 10B
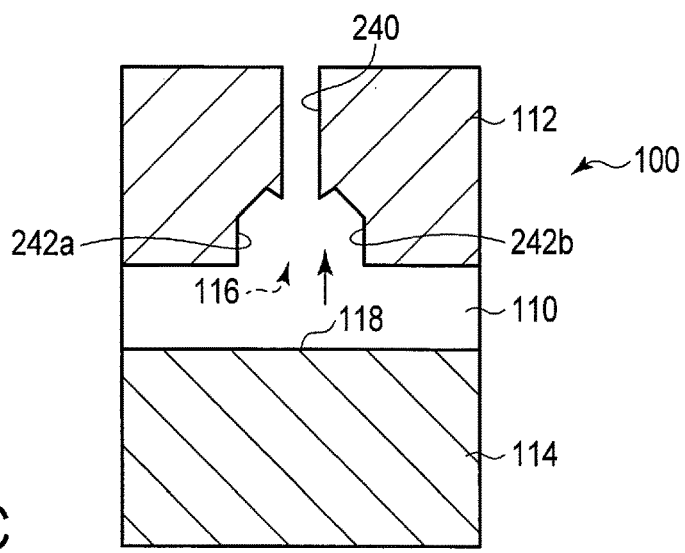
F I G. 10C

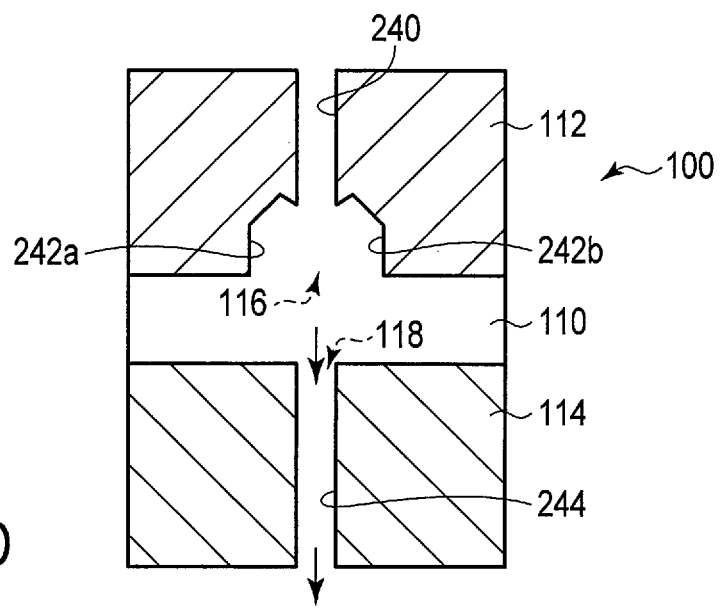
F I G. 10D
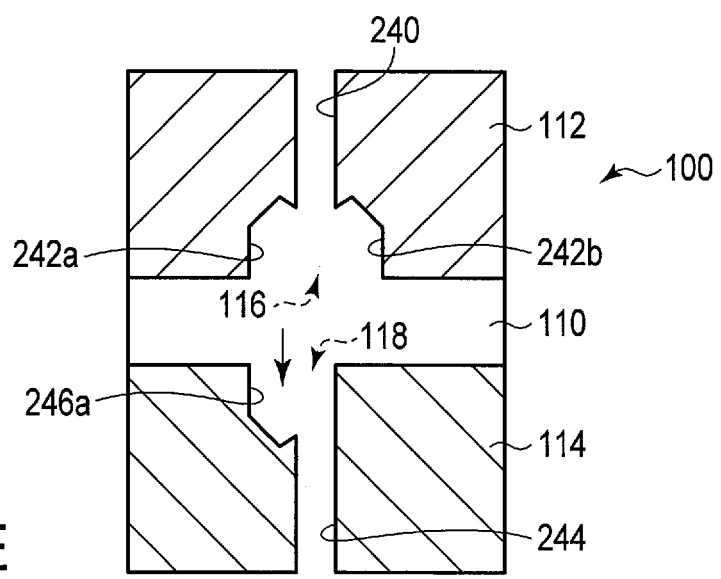
F I G. 10E

SURGICAL PROCEDURE OF KNEE JOINT

This is a Division of application Ser. No. 15/337,596 filed Oct. 28, 2016. The disclosure of the prior application is hereby incorporated by reference herein in its entirety.

BACKGROUND OF THE INVENTION

1. Field of the Invention

This invention relates to a surgical procedure of a knee joint which is performed under an arthroscope.

2. Description of the Related Art

In a case where a surgeon performs reconstruction of a ligament in a knee joint, it is known that an outer shape of a cross section of an implanted tendon which is perpendicular to a longitudinal axis thereof, is a polygonal shape such as a rectangular shape, an elliptical shape, or an approximately polygonal shape close to the elliptical shape.

BRIEF SUMMARY OF THE INVENTION

According to one aspect of the present invention, a surgical procedure of preparing bone holes to dispose an implanted tendon to a femur when performing reconstruction of a ligament in a knee joint, includes: forming a first bone hole in the femur; and applying ultrasonic vibration from a treatment portion of an ultrasonic treatment instrument to the femur, thereby cutting and expanding the first bone hole from the inside of the knee joint to the first bone hole of the femur along a predetermined depth, and forming a second bone hole having a polygonal shape, an approximately polygonal shape, an elliptical shape or an approximately elliptical shape to receive the implanted tendon.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view showing a treatment system for use in a surgical treatment of a knee joint;

FIG. 4A is a schematic partial cross-sectional view showing a state where a hole is formed in a bone with the ultrasonic probe shown in FIG. 3A;

FIG. 4B is a schematic perspective view showing a concave hole formed in a desired orientation at a desired position of a footprint region of an anterior cruciate ligament with the ultrasonic probe shown in FIG. 4A;

FIG. 5A is a schematic perspective view showing a modification of a treatment portion of the ultrasonic probe shown in FIG. 3A;

FIG. 5B is a schematic perspective view showing a modification of the treatment portion of the ultrasonic probe shown in FIG. 3A;

FIG. 6A is a schematic perspective view showing a modification of the treatment portion of the ultrasonic probe shown in FIG. 3A;

FIG. 6B is a schematic perspective view showing a modification of the treatment portion of the ultrasonic probe shown in FIG. 3A;

FIG. 6C is a schematic perspective view showing a modification of the treatment portion of the ultrasonic probe shown in FIG. 3A;

FIG. 8D is a schematic view showing a state where a concave hole is formed from the inside of the joint to the through hole of the tibia in the state shown in FIG. 8C with the probe of the ultrasonic treatment instrument;

FIG. 8E is a schematic view showing a state where the implanted tendon including the STG tendon shown in FIG. 7 is fixed to the femur and the tibia;

FIG. 10A is a schematic view showing a procedure of the reconstruction of the anterior cruciate ligament and showing a state where a through hole (a drilled hole) is formed from the inside of the knee joint to the footprint region of the anterior cruciate ligament of the femur of the knee joint with the drill;

FIG. 10B is a schematic view showing a state where a concave hole is formed from the inside of the joint at a position including the through hole of the femur in the state shown in FIG. 10A with the probe of the ultrasonic treatment instrument;

FIG. 10C is a schematic view showing a state where a concave hole is formed from the inside of the joint at a position that is adjacent to the concave hole of the femur in the state shown in FIG. 10B and that includes the through hole of the femur with the probe of the ultrasonic treatment instrument;

FIG. 10D is a schematic view showing a state where a through hole (a drilled hole) is formed from the inside of the knee joint to the footprint region of the anterior cruciate ligament of the tibia of the knee joint in the state shown in FIG. 10C with the drill;

FIG. 10E is a schematic view showing a state where a concave hole is formed from the inside of the joint at a position including the through hole of the tibia in the state shown in FIG. 10D with the probe of the ultrasonic treatment instrument;

DETAILED DESCRIPTION OF THE INVENTION

Figure 2:
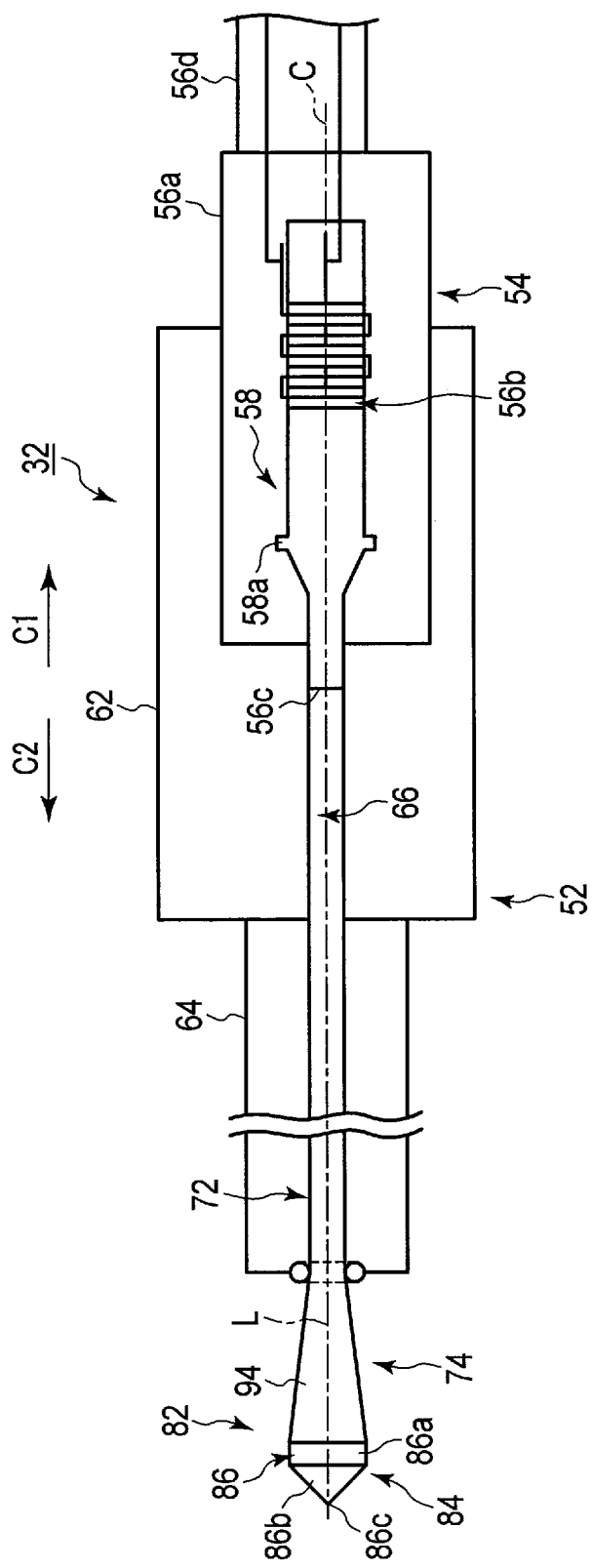
FIG. 2 is a schematic view showing one example of an ultrasonic treatment unit for use in the system shown in FIG. 1.

Embodiments of this invention will be described with reference to the drawings.

When a knee joint 100 is treated, for example, a treatment system 10 shown in FIG. 1 is used. The treatment system 10 includes an arthroscope device 12, a treatment device 14, and an irrigation device 16.

The arthroscope device 12 includes an arthroscope 22 to observe an inner part of the knee joint 100, i.e., the inside of a joint cavity 110 of a patient, an arthroscope controller 24 that performs image processing on the basis of a subject image imaged by the arthroscope 22, and a monitor 26 that displays the image generated by the image processing in the arthroscope controller 24. The arthroscope 22 is inserted into the joint cavity 110 of the knee joint 100 through a first portal 102 by a skin cutting portion via which the inner part of the knee joint 100 of the patient communicates with an outer side of skin. A position of the first portal 102 is not uniform but is suitably determined in accordance with a patient's condition. It is also preferable that an unshown cannula is disposed to the first portal 102 and the arthroscope 22 is inserted into the joint cavity 110 of the knee joint 100 via the cannula. Additionally, it is drawn that the arthroscope 22 and a later-described treatment instrument 52 of the treatment device 14 are disposed to face each other in FIG. 1, but the arthroscope and the treatment instrument are arranged in a suitable positional relation in accordance with a position of a treatment object, or the like.

The treatment device 14 includes a first treatment unit 30, a second treatment unit 32, a controller 34, and switches 36a and 36b. The switches 36a and 36b are shown as hand switches in FIG. 1, but may be foot switches.

The controller 34 suitably supplies energy (electric power) to the first treatment unit 30 in accordance with an operation of the switch 36a to form a hole in a bone B. The first treatment unit 30 is, for example, a drill.

The controller 34 suitably supplies energy (electric power) to a later-described ultrasonic transducer unit 54 of the second treatment unit 32 in accordance with an operation of the switch 36b to transmit ultrasonic vibration to a treatment portion 74 of a later-described probe 66 of the second treatment unit 32. The treatment portion 74 of the probe 66 is inserted into the joint cavity 110 of the knee joint 100 through a second portal 104 by a skin cutting portion via which the inner part of the joint 100 of the patient communicates with the outer side of skin. A position of the second portal 104 is not uniform but is suitably determined in accordance with the patient's condition. It is also preferable that an unshown cannula is disposed to the second portal 104 and the treatment portion 74 of the probe 66 is inserted into the joint cavity 110 of the knee joint 100 via the cannula. The switch 36b maintains, for example, a driven state of a later-described ultrasonic transducer 56b in a state where the switch is pressed to be operated, and when the pressed state is released, the driven state of the ultrasonic transducer 56b is released.

Here, it is described that one switch 36b is disposed, but the switches may be disposed. An amplitude of the ultrasonic transducer 56b can suitably be set by the controller 34. In consequence, a frequency of the ultrasonic vibration to be output from the later-described ultrasonic transducer 56b is the same, but by the operation of the switch 36b, the amplitude may vary. Therefore, it is also preferable that the switch 36b can switch the amplitude of the ultrasonic transducer 56b to states such as two large and small states.

Additionally, although not shown in the drawing, it is also preferable that as the treatment device 14, there is used another treatment unit that dissects a later-described region to which an anterior cruciate ligament adheres. In this way, in the treatment device 14, treatment units are suitably used.

The irrigation device 16 includes a liquid source 42 that contains an irrigation liquid such as physiological saline, an irrigation pump unit 44, a liquid supply tube 46 whose one end is connected to the liquid source 42, a liquid discharge tube 48, and a suction bottle 50 connected to one end of the liquid discharge tube 48. The suction bottle 50 is connected to a suction source attached to a wall of an operating room. In the irrigation pump unit 44, the irrigation liquid can be supplied from the liquid source 42 by a liquid supply pump 44a. Additionally, in the irrigation pump unit 44, suction/suction stop of the irrigation liquid in the joint cavity 110 of the knee joint 100 to the suction bottle 50 can be switched by opening/closing a pinching valve 44b as a liquid discharge valve.

The other end of the liquid supply tube 46 which is a liquid supply tube path is connected to the arthroscope 22. In consequence, the irrigation liquid can be supplied into the joint cavity 110 of the joint 100 via the arthroscope 22. The other end of the liquid discharge tube 48 which is a liquid discharge tube path is connected to the arthroscope 22. In consequence, the irrigation liquid can be discharged from the joint cavity 110 of the joint 100 via the arthroscope 22. Additionally, needless to say, the other end of the liquid discharge tube 48 may be connected to the treatment instrument 52, so that the irrigation liquid can be discharged from the joint 100. It is to be noted that the irrigation liquid can be supplied and discharged through another portal.

As shown in FIG. 2, the second treatment unit 32 has the ultrasonic treatment instrument 52 and the ultrasonic transducer unit 54. It is preferable that the ultrasonic transducer unit 54 is attachable to and detachable from the ultrasonic treatment instrument 52, but the unit may be integrated with the ultrasonic treatment instrument. The ultrasonic transducer unit 54 has a housing (a transducer case) 56a, the bolt-clamped Langevin-type transducer 56b, and a connecting portion 56c at a proximal end of the later-described ultrasonic probe 66. The connecting portion 56c is formed at a distal end of the transducer 56b. It is preferable that the connecting portion 56c projects along a central axis C of the ultrasonic transducer unit 54 toward a distal side of the housing 56a. A cable 56d having one end connected to the transducer 56b and the other end connected to the controller 34 extends out from a proximal end of the housing 56a of the ultrasonic transducer unit 54. The transducer 56b and the connecting portion 56c form an integrated vibrating body 58.

The housing 56a supports a supported portion 58a of the vibrating body 58. The ultrasonic transducer unit 54 is known and thus a detailed description is omitted. In a state where vibration is generated in the transducer 56b, the connecting portion 56c and a proximal end of the transducer 56b constitute antinodes of the vibration. It is to be noted that although not shown in FIG. 2, the switch 36b is preferably disposed in the housing 56a of the ultrasonic transducer unit 54 or in a later-described housing 62 of the ultrasonic treatment instrument 52.

The ultrasonic treatment instrument 52 includes the housing (a handle) 62, a tubular body (an outer tube) 64 extending out from the housing 62 along the central axis C, and the ultrasonic probe 66 inserted into the tubular body 64. Here, in the ultrasonic treatment instrument 52, a side on which the housing 62 is positioned relative to the tubular body 64 is defined as a proximal side (an arrow C1 side), and a side opposite to the proximal side is defined as a distal side (an arrow C2 side). The tubular body 64 is attached to the housing 62 from the distal side. Furthermore, the ultrasonic treatment instrument 52 has the later-described treatment portion 74 in a portion on the distal side to the tubular body 64.

The housing 62 and the tubular body 64 of the ultrasonic treatment instrument 52 are made of a material having insulating properties. The housing 56a of the ultrasonic transducer unit 54 is attachably/detachably connected to the housing 62 of the ultrasonic treatment instrument 52. It is also preferable that the housing 62 of the ultrasonic treatment instrument 52 and the housing 56a of the ultrasonic transducer unit 54 are integrated.

A rotary knob (not shown) of a rotary operating member may be attached to the housing 62 of the treatment instrument 52. The rotary knob is rotatable relative to the housing 62 in a periaxial direction of the central axis of the tubular body 64. By the rotation of the rotary knob, the housing 56a of the ultrasonic transducer unit 54, the tubular body 64, the later-described treatment portion 74 and a probe main body portion 72 rotate together relative to the housing 62 in the periaxial direction of the central axis C of the probe main body portion 72.

Outer peripheral surfaces of the housing 62 and the tubular body 64 of the ultrasonic treatment instrument 52 have insulating properties. The ultrasonic probe 66 is made of a material that is capable of transmitting the ultrasonic vibration, e.g., a metal material such as a titanium alloy material. At the proximal end of the probe 66, there is fixed the connecting portion 56c of the ultrasonic transducer unit 54 that is fixed to the housing 62. It is preferable that a total length of the probe 66 is, for example, an integer multiple of a half-wave length based on a resonance frequency of the transducer 56b. The total length of the probe 66 is not limited to the integer multiple of the half-wave length based on the resonance frequency of the transducer 56b, and is suitably adjusted in accordance with the material, an amplitude enlargement ratio, or the like. Therefore, the total length of the probe 66 may be an approximate integer multiple of the half-wave length based on the resonance frequency of the transducer 56b. In the vibrating body 58 and the probe 66, materials or lengths thereof are suitably set to vibrate as a whole at the resonance frequency of the transducer 56b and a frequency in an output of the controller 34.

Figure 3A:
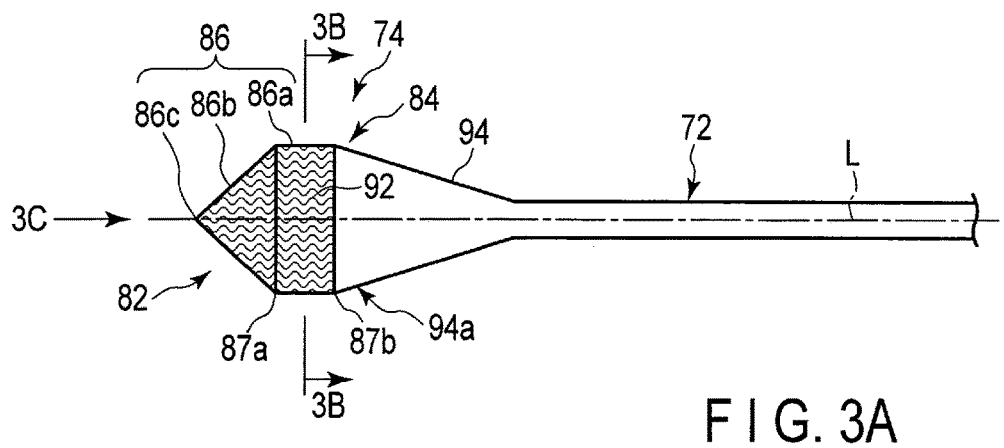
FIG. 3A is a schematic view showing an ultrasonic probe of a treatment instrument shown in FIG. 2.

As shown in FIG. 2 and FIG. 3A, the ultrasonic probe 66 includes the probe main body portion 72, and includes the treatment portion 74 that is disposed on the distal side of the probe main body portion 72 and that is capable of forming a hole in a bone of a treatment object by the ultrasonic vibration. The ultrasonic vibration generated in the ultrasonic transducer 56b is transmitted to the probe main body portion 72 via the connecting portion 56c of the vibrating body 58. The ultrasonic vibration generated in the ultrasonic transducer 56b is transmitted to the treatment portion 74 via the connecting portion 56c and the probe main body portion 72.

It is preferable that the probe main body portion 72 is formed straight. It is preferable that the treatment portion 74 extends straight out from a distal end of the probe main body portion 72 on the distal side, but the treatment portion 74 may suitably be bent in consideration of visibility of the treatment portion 74 to the arthroscope 22. Therefore, the central axis C of the probe main body portion 72 may match a longitudinal axis L of the treatment portion 74 or may be different therefrom.

The treatment portion 74 includes a cutting portion 82. As a projection shape when the proximal side is seen from the distal side along the longitudinal axis L of the treatment portion 74, the cutting portion 82 has a polygonal shape such as a rectangular shape shown in FIG. 3B and FIG. 3C or an elliptical shape (including an approximately elliptical shape) shown in FIG. 3D and FIG. 3E. The projection shape may be an approximately polygonal shape close to the elliptical shape. The polygonal shape may be a regular polygon. The projection shape may be an approximately polygonal shaped rectangle having round corners, or an approximately elliptical shape such as a track shape of an athletic field. For this reason, the projection shape is formed into a suitable shape such as the polygonal shape such as the approximately polygonal shape, the elliptical shape, or the approximately elliptical shape.

As shown in FIG. 4A, the cutting portion 82 of the treatment portion 74 is moved so that the treatment portion 74 applies a force F to a bone B on the distal side along the longitudinal axis L in a state where the ultrasonic vibration is transmitted to the probe main body portion 72. Because of this, the probe 66 is moved straight or generally straight to the distal side along the central axis C. At this time, the bone is resected with the treatment portion 74.

The cutting portion 82 includes a block body 86 in a distal portion of the treatment portion 74. The block body 86 is formed into a block shape to determine an outer shape (a contour of the hole) when the bone B is resected. The block body 86 has a pillar-shaped portion 86a, and a convex portion 86b projecting out from the pillar-shaped portion 86a to the distal side along the longitudinal axis L. The pillar-shaped portion 86a is formed into a shape of a pillar such as a polygonal pillar or an elliptical pillar. The pillar-shaped portion 86a and the convex portion 86b are integrally formed by cut processing or the like.

A cross section of the pillar-shaped portion 86a of the block body 86 of the cutting portion 82 which is perpendicular to the longitudinal axis L is formed into the same shape or approximately the same shape from a distal end 87a to a proximal end 87b along the longitudinal axis L. An outer peripheral surface of the pillar-shaped portion 86a is continuous with the proximal side of the distal end 87a of the pillar-shaped portion 86a along the longitudinal axis L.

Therefore, the cross section of the pillar-shaped portion 86a, which is perpendicular to the longitudinal axis L, is formed into the same area or approximately the same area from the distal end 87a to the proximal end 87b. The distal end 87a of the pillar-shaped portion 86a determines a maximum outer shape region (the contour of the hole) when the bone B is resected. The outer peripheral surface of the pillar-shaped portion 86a has the same projection shape as the projection shape of the cutting portion 82 when its proximal side is seen from the distal side along the longitudinal axis L of the treatment portion 74. In this way, an outer shape of the cutting portion 82 of the treatment portion 74 is formed in accordance with a shape of the hole to be formed by resecting the bone B (see FIG. 4B).

A polygonal pillar of the pillar-shaped portion 86a is formed into a suitable shape or a shape close to the suitable shape, e.g., a triangular pillar, a quadrangular pillar, a pentangular pillar, a hexagonal pillar or the like. In the pillar-shaped portion 86a, distinct corners do not necessarily have to be formed. Furthermore, the distal end 87a of the pillar-shaped portion 86a does not have to be a regular polygon, and is also preferably formed to be flat. Therefore, the hole can be formed into a desire shape by use of the probe 66 according to the present embodiment.

Figure 3B:
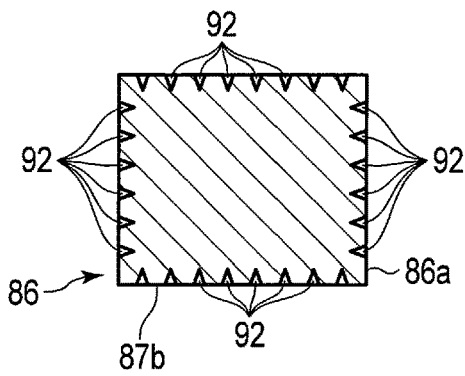
FIG. 3B is a cross-sectional view showing a state where the ultrasonic probe shown in FIG. 3A is cut along the 3B-3B line perpendicular to a longitudinal axis in FIG. 3A.
Figure 3C:
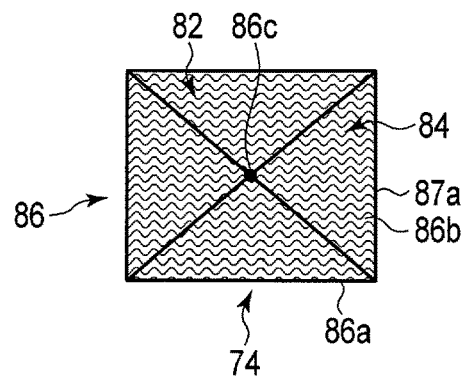
FIG. 3C is a schematic view showing a state where the ultrasonic probe shown in FIG. 3A is seen from a direction indicated by an arrow 3C in FIG. 3A.
Figure 3D:
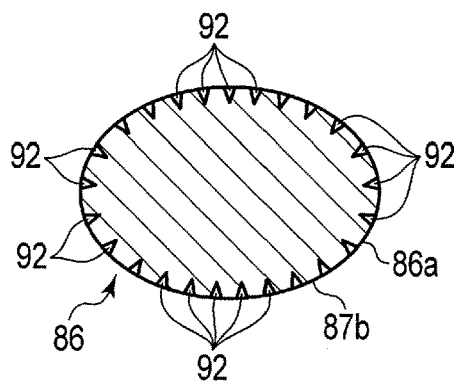
FIG. 3D is a cross-sectional view showing a modification of the ultrasonic probe shown in FIG. 3A and cut along the 3B-3B line perpendicular to the longitudinal axis in FIG. 3A.
Figure 3E:
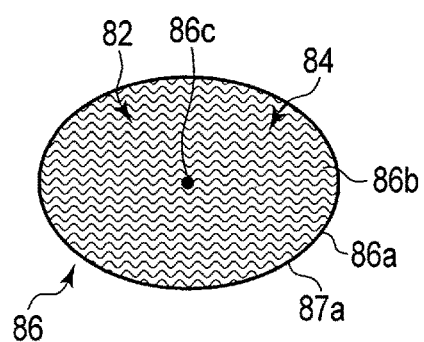
FIG. 3E is a schematic view showing a modification of the ultrasonic probe shown in FIG. 3A and seen from the direction indicated by the arrow 3C in FIG. 3A.

It is preferable that the projection shape of the cutting portion 82 is a polygonal shape such as an approximately rectangular shape shown in FIG. 3B and FIG. 3C, or the elliptical shape shown in FIG. 3D and FIG. 3E. In a case of performing reconstruction of the anterior cruciate ligament by use of a later-described STG tendon 212 (see FIG. 7), an outer shape of a cross section of an implanted tendon which is perpendicular to the longitudinal axis is formed as an approximately rectangular shape of about 4 mm×5 mm. Because of this, in a case where, as one example, the projection shape of the cutting portion 82 is an approximately rectangular shape, it is preferable that a size of the outer shape of the cross section perpendicular to the longitudinal axis L is, for example, about 4 mm×5 mm.

The convex portion 86b is formed on the distal side of the pillar-shaped portion 86a. The convex portion 86b projects out from the distal end 87a of the pillar-shaped portion 86a to the distal side along the longitudinal axis L, and is formed into a conical shape or an approximately conical shape based on the projection shape of the cutting portion 82. A top portion 86c of the convex portion 86b of the cutting portion 82 is formed at a suitable position on the distal side along the longitudinal axis L to the pillar-shaped portion 86a. The top portion 86c of the convex portion 86b of the cutting portion 82 is formed in a range of a projection shape of a boundary (the distal end 87a of the pillar-shaped portion 86a) between the convex portion of the cutting portion 82 and the pillar-shaped portion 86a thereof when the proximal side is seen from the distal side along the longitudinal axis L. A line connecting one point of the boundary between the convex portion 86b of the cutting portion 82 and the pillar-shaped portion 86a of the cutting portion 82 to the top portion 86c may be a straight line or a curved line. Therefore, the convex portion 86b of the cutting portion 82 is not limited to the conical shape and may have the approximately conical shape. Furthermore, the top portion 86c does not have to be sharpened and may have an obtuse shape.

Here, it is defined that the convex portion 86b of the cutting portion 82 is formed as a quadrangular pyramid shown in FIG. 3C. A contact area between the top portion 86c of the convex portion 86b of the cutting portion 82 and the bone is small in an initial state when the bone is resected.

Because of this, the bone can start to be cut in a state where friction between the cutting portion 82 and the bone is decreased.

Here, the top portion 86c at the topmost end of the convex portion 86b of the cutting portion 82 is appropriately sharp. When the top portion 86c is brought into contact with or pressed onto the bone B with suitable force, it is difficult for the top portion to slip to the bone B as compared with the obtuse shape. For this reason, when the ultrasonic vibration is transmitted to the probe 66 in the state where the top portion 86c is brought into contact with or pressed onto the bone B with suitable force, it is difficult for the top portion to slip to the bone B, and for the position to shift in a case where a hole 200 (see FIG. 4A and FIG. 4B) starts to be opened. Therefore, when the top portion 86c is appropriately sharp, it is difficult for the position of the top portion 86c at the topmost end of the convex portion 86b of the cutting portion 82 to shift to the bone B, and it becomes easy to determine a position at which the hole 200 is to be formed.

As shown in FIG. 3A to FIG. 3C, the treatment portion 74 includes a discharging portion 84 to discharge cutting debris of the bone resected by the cutting portion 82 from the cutting portion 82 toward the proximal side along the longitudinal axis L. Apart of the discharging portion 84 is disposed in the cutting portion 82. The discharging portion 84 includes concave portions 92 formed in an outer peripheral surface of the cutting portion 82 and a shaft portion 94 disposed on the proximal side of the cutting portion 82.

As shown in FIG. 3B, in the outer peripheral surface of the cutting portion 82, there are formed the concave portions 92 of the discharging portion 84 that decreases the contact area between the treatment portion 74 and the bone, and which becomes a discharge path of the cutting debris. Here, each of the concave portions 92 is formed into a wavelike shape having a bottom surface at a position dented to outer peripheral surfaces of the pillar-shaped portion 86a and the convex portion 86b. The bottom surface of the concave portion 92 is closer to the central axis C (the longitudinal axis L) than the pillar-shaped portion 86a. The concave portions 92 do not necessarily have to be formed in the convex portion 86b (see FIG. 5A).

The shaft portion 94 is extended from the block body 86 of the cutting portion 82 to the proximal side along the longitudinal axis L. The shaft portion 94 is interposed between the distal end of the probe main body portion 72 and the proximal end 87b of the block body 86 of the cutting portion 82. A projection shape of the shaft portion 94 when its proximal side is seen from the distal side along the longitudinal axis L falls within a range of a projection shape of the block body 86 of the cutting portion 82.

The shaft portion 94 has a distal portion 94a that is continuous with a proximal end of the block body 86. In the distal portion 94a of the shaft portion 94, a cross-sectional area of a cross section perpendicular to the longitudinal axis L decreases from the distal side toward the proximal side along the longitudinal axis L. The shaft portion 94 also has a range in which the cross-sectional area of the cross section perpendicular to the longitudinal axis L increases from the distal side toward the proximal side, or is maintained to be constant in a range on the proximal side of the distal portion 94a. That is, the shaft portion 94 has a narrowed range between its distal end and its proximal end. A boundary between the distal portion 94a of the shaft portion 94 and the proximal end of the block body 86 (the distal end 87a of the pillar-shaped portion 86a) has a shape to prevent stress concentration in a state where the ultrasonic vibration is transmitted. Therefore, a boundary between the distal portion 94a of the shaft portion 94 and the proximal end 87b of the pillar-shaped portion 86a of the block body 86 is smoothly continuous. Note that when the treatment portion 74 is seen from the distal side toward the proximal side along the longitudinal axis L, the shaft portion 94 is hidden behind the block body 86 and cannot be observed. Therefore, the shaft portion 94 that is continuous with the proximal side of the block body 86 can be a part of the discharging portion 84 to discharge the cutting debris of the bone or a liquid such as an irrigation liquid to the proximal side along the longitudinal axis L.

When the treatment portion 74 is seen from the distal side to the proximal side in a direction indicated by an arrow 3C in FIG. 3A, in other words along the longitudinal axis L, outer shapes of the convex portion 86b of the cutting portion 82 and the pillar-shaped portion 86a thereof are observed as an outer shape of the treatment portion 74 as shown in FIG. 3C. At this time, the concave portions 92 of the discharging portion 84 are formed in the pillar-shaped portion 86a, but in an outer edge of the treatment portion 74 in FIG. 3C, the outer peripheral surface of the pillar-shaped portion 86a appears at least once between the distal end 87a of the pillar-shaped portion 86a and the proximal end 87b thereof. Therefore, the cutting portion 82 determines the maximum outer shape region. Accordingly, when the proximal side is seen from the distal side along the longitudinal axis L, the projection shape of the cutting portion 82 forms the shape of the hole when the bone B is resected by using the treatment instrument 52.

The concave hole 200 of the desired shape has, for example, an opening edge 202 of the same shape and size as in the projection shape of the cutting portion 82 of the treatment portion 74 when the proximal side is seen from the distal side along the longitudinal axis L, and the concave hole is dented straight to an inner side in the same shape as the shape of the opening edge 202. Therefore, one example of the desired shape of the hole 200 is a rectangular shape having a suitable depth.

Next, an operation of the treatment system 10 according to this embodiment will be described. Here, there will be described a case where the concave hole 200 is formed in the bone B by use of the ultrasonic probe 66 of the second treatment unit 32 after a through hole or a concave hole is formed in a femur 112.

The ultrasonic transducer unit 54 is attached to the ultrasonic treatment instrument 52 to form the second treatment unit 32. At this time, the proximal end of the ultrasonic probe 66 is connected to the connecting portion 56c of the ultrasonic transducer unit 54. Here, for the purpose of simplifying the description, it is defined that the central axis C of the probe main body portion 72 matches the longitudinal axis L of the treatment portion 74.

When the switch 36b is operated, the controller 34 supplies energy to the ultrasonic transducer 56b of the vibrating body 58 fixed to the proximal end of the ultrasonic probe 66, to generate the ultrasonic vibration in the ultrasonic transducer 56b. Because of this, the ultrasonic vibration is transmitted to the ultrasonic probe 66 via the vibrating body 58. This vibration is transmitted from the proximal end of the ultrasonic probe 66 toward the distal side. At this time, the connecting portion 56c at a distal end of the vibrating body 58 and a proximal end of the vibrating body 58 are antinodes of the vibration. One point on the central axis C on an inner side of the supported portion 58a is a node of the vibration. The proximal end of the ultrasonic probe 66 which is connected to the connecting portion 56c of the vibrating body 58 is an antinode of the vibration, and the cutting portion 82 of the treatment portion 74 is an antinode of the vibration.

The cutting portion 82 of the treatment portion 74 is the antinode of the vibration, so the cutting portion 82 is displaced along the longitudinal axis L at a rate (e.g., several thousand m/s) based on the resonance frequency of the transducer 56b. Therefore, when the treatment instrument 52 is moved toward the distal side along the longitudinal axis L (the central axis C) to press the treatment portion 74 onto the bone B in the state where the vibration is transmitted, a region of the bone B which is in contact with the treatment portion 74 is shattered by an operation of the ultrasonic vibration. Therefore, as the treatment instrument 52, i.e., the probe 66 moves toward the distal side along the longitudinal axis L (the central axis C), the concave hole 200 is formed in the bone B along the longitudinal axis L of the treatment portion 74 of the ultrasonic probe 66.

Here, the top portion 86c at the topmost end of the convex portion 86b of the cutting portion 82 is appropriately sharp. When the top portion 86c is brought into contact with or pressed onto the bone B with suitable force, it is difficult for the top portion 86c to slip to the bone B as compared with the obtuse shape. Because of this, when the ultrasonic vibration is transmitted to the probe 66 in the state where the top portion 86c is brought into contact with or pressed onto the bone B with suitable force, it is difficult for the top portion to slip to the bone B and to shift in the case of starting opening the hole 200 (see FIG. 4A and FIG. 4B). Therefore, when the top portion 86c is suitably sharp, it is difficult for the position of the top portion 86c at the topmost end of the convex portion 86b of the cutting portion 82 to shift to the bone B, and it becomes easy to determine the position where the hole 200 is to be formed.

Additionally, in a case where the bone B is present under a cartilage, when the treatment portion 74 of the ultrasonic probe 66 is pressed onto the cartilage toward the distal side along the longitudinal axis L, a region of the cartilage which is in contact with the treatment portion 74 is excised by the operation of the ultrasonic vibration, and a concave hole is formed in the cartilage.

The concave portions 92 of the discharging portion 84 are respectively formed in the convex portion 86b and the pillar-shaped portion 86a of the treatment portion 74 of the ultrasonic probe 66. The concave portions 92 of the discharging portion 84 are formed whereby, in the case where the concave hole 200 is formed in the bone B, the contact area between the cutting portion 82 and the bone B is smaller than in a case where the concave portions 92 are not formed. Thus, the friction between the cutting portion 82 and the bone B is decreased to inhibit generation of frictional heat in the treatment portion 74 and the bone B. Also, due to the presence of the concave portions 92, a surface area of the cutting portion 82 increases as compared with the case where the concave portions 92 are not formed. A joint liquid or the irrigation liquid is present in the joint 100, and thus in the treatment portion 74, a heat radiation ability improves due to the presence of the concave portions 92, and the treatment portion is suitably cooled. Furthermore, the cutting debris of the bone B is disposed in the concave portions 92. The concave portions 92 are continuous from the distal end 87a of the pillar-shaped portion 86a to the proximal end 87b thereof. Because of this, the cutting debris of the bone B, once entering the concave portions 92, moves along the concave portions 92 which are continuous from the distal end 87a of the pillar-shaped portion 86a to the proximal end 87b thereof. Therefore, the cutting debris of the bone B is easily discharged to the proximal side of the treatment portion 74 through the distal end 87a of the pillar-shaped portion 86a and the proximal end 87b thereof. Thus, the treatment portion 74 of the treatment unit 32 is capable of forming the concave hole 200 at the suitable rate.

When the proximal side of the treatment portion 74 is seen from the distal side along the longitudinal axis L, the shaft portion 94 of the discharging portion 84 cannot be observed due to the presence of the pillar-shaped portion 86a of the cutting portion 82. Therefore, when forming the concave hole 200, a space is formed between the proximal end 87b of the pillar-shaped portion 86a, the shaft portion 94, and a lateral surface of the bone hole 200. Therefore, the cutting debris of the bone B is discharged from the proximal end 87b of the pillar-shaped portion 86a toward the space between the shaft portion 94 and the lateral surface of the bone hole 200.

In this way, the cutting debris of a region of the bone B which is treated with the treatment portion 74 is discharged to the proximal side through the concave portions 92 of the discharging portion 84 along the longitudinal axis L. In particular, the inside of the joint 100 is filled with the joint liquid. Furthermore, in the joint 100, the irrigation liquid circulates. Because of this, the joint liquid or the irrigation liquid becomes a lubricant to easily discharge the cutting debris of the bone B from the cutting portion 82 to the proximal side along the longitudinal axis L. In the case where the concave hole 200 is formed to the desired depth in the bone B, the pressed switch 36b is released to stop the generation of the ultrasonic vibration. Then, the ultrasonic probe 66 is moved to the proximal side along the longitudinal axis L.

As shown in FIG. 4B, the concave hole 200 formed in the bone B is formed into the same shape as that of an outer edge of the pillar-shaped portion 86a of the cutting portion 82 from the inlet 202 of the hole to an inner region 204. An innermost position 206 of the concave hole 200 is formed into the same shape as that of an outer shape of the convex portion 86b including the top portion 86c. That is, as shown in FIG. 4A, in a case where the ultrasonic vibration is transmitted to the probe 66 of the ultrasonic treatment instrument 52 to form the concave hole 200 in the bone B, the shape of the cutting portion 82 of the treatment portion 74 can be copied.

The pillar-shaped portion 86a of the cutting portion 82 of the probe 66 maintains a region constituting the maximum outer shape region from the distal end 87a to the proximal end 87b, and imparts a certain degree of length along the longitudinal axis L. That is, an outer shape of the pillar-shaped portion 86a from the distal end 87a toward the proximal end has a certain degree of length parallel to the longitudinal axis L. Therefore, when the probe 66 is moved straight along the longitudinal axis L, the hole 200 can be formed straight along the longitudinal axis L with the pillar-shaped portion 86a of the cutting portion 82.

The ultrasonic vibration is transmitted to the probe 66 of the treatment unit 32 according to this embodiment, and the ultrasonic vibration is applied to a region of the bone B in which the hole is to be formed, whereby the region of the bone B, which is in contact with the cutting portion 82 of the treatment portion 74 at a distal end of the probe 66, is finely shattered and cut. The distal portion of the treatment portion 74 is formed into a convex shape (the convex portion 86b), and additionally, the concave portions 92 of the discharging portion 84 to discharge the cutting debris of the bone B are formed in the cutting portion 82. For this reason, as compared with the cutting portion 82 which does not have the convex portion 86*b* and keeps the projection shape of the pillar-shaped portion 86*a* in an axial direction, the cutting portion having the convex portion 86*b* and the concave portions 92 of the discharging portion 84 can proceed with a hole opening processing earlier.

The cutting portion 82 is moved along the longitudinal axis L, so that the shape of the distal end 87*a* of the pillar-shaped portion 86*a* when the treatment portion 74 is seen from the distal side along the longitudinal axis L can be copied to the opening edge of the concave hole 200. Because of this, the projection shape of the cutting portion 82 along the longitudinal axis L is the same as the desired shape of the concave hole 200. The bone B is further dug with the cutting portion 82, so that the concave hole 200 having the desired shape and desired depth can be opened in the bone B.

In addition, the distal portion of the treatment portion 74 is formed into a convex shape (the convex portion 86*b*), and due to the concave portions 92 of the discharging portion 84, the contact area between the bone B and the cutting portion 82 decreases, whereby the cutting debris is further easily discharged to the proximal side of the cutting portion 82. Therefore, when cutting the bone B, it is possible to inhibit the generation of the frictional heat between the treatment portion 74 and the bone B and to increase a processing rate.

It is to be noted that the treatment portion 74 of the probe 66 of the ultrasonic treatment instrument 52 is not limited to the treatment portion shown in FIG. 2A, and various shapes such as the shapes shown in FIG. 5A to FIG. 6C are allowed.

In an example shown in FIG. 5A, a shape of the concave portion 92 of the discharging portion 84 of the treatment portion 74 is different from that of the discharging portion 84 of the treatment portion 74 shown in FIG. 2.

In an example shown in FIG. 5B, the discharging portion 84 of the treatment portion 74 is not present.

In an example shown in FIG. 6A, the number of the top portions 86*c* of the treatment portion 74 is plural (three).

In an example shown in FIG. 6B, the number of the top portions 86*c* of the treatment portion 74 is plural (two).

In an example shown in FIG. 6C, the convex portion 86*b* of the cutting portion 82 is formed into a hemispherical shape. It is preferable that a size of the convex portion 86*b* is the same as or slightly smaller than a hole diameter of a hole (a drilled hole) formed with the drill 30. In the treatment portion 74 of the example shown in FIG. 6C, the ultrasonic vibration is transmitted to the convex portion 86*b* inserted in the drilled hole. The convex portion 86*b* is guided to the drilled hole, and by use of the drilled hole as a guide hole, the concave hole 200 (see FIG. 4B) is formed straighter.

A first procedure example will be described with reference to FIG. 7 and FIG. 8A to FIG. 8E. FIG. 8A to FIG. 8E schematically show a state where the femur 112, a tibia 114, and the joint cavity 110 of the knee joint 100 are seen from the anterior side. Arrows in FIG. 8A to FIG. 8D indicate a bone excising direction (a moving direction of the probe 66 along the longitudinal axis L).

Figure 7:
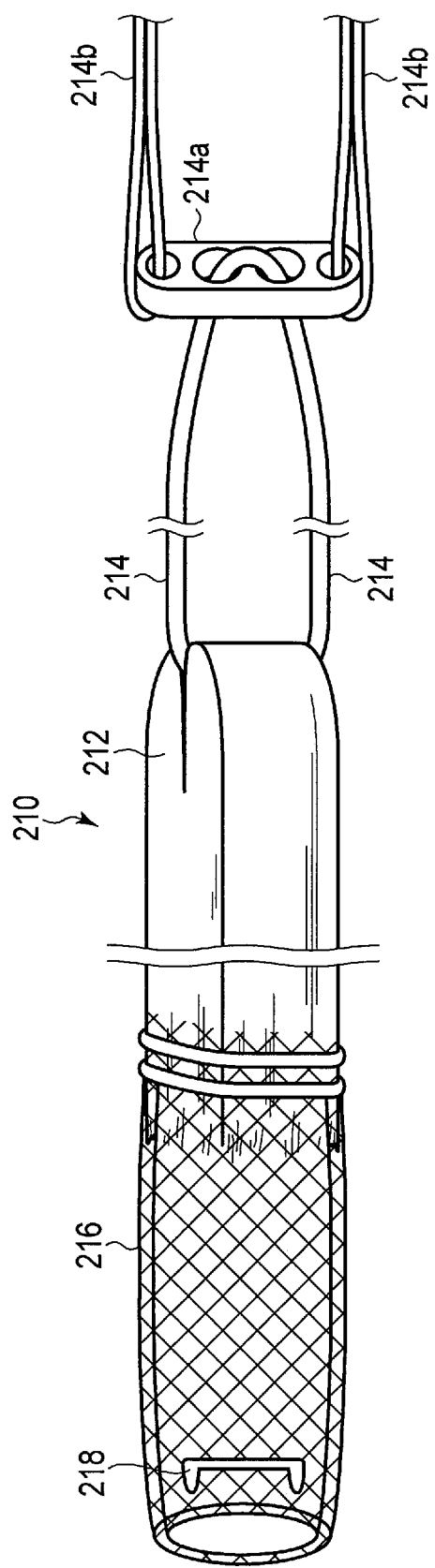
FIG. 7 is a schematic view of an implanted tendon which includes an STG tendon for use in reconstruction of the anterior cruciate ligament.

Here, an example is described where a semitendinosus tendon or a gracilis tendon that is present on an inner side of the knee is used as the implanted tendon. This implanted tendon is referred to as the STG tendon. As shown in FIG. 7, the STG tendon as the implanted tendon is folded several times to be formed to a suitable length as a part of the implanted tendon 210. The implanted tendon 210 has the STG tendon 212, a suspension fixture 214*a* disposed at one end of the STG tendon 212 via suture threads 214 and, for example, a pair of artificial ligaments 216 fixed to the other end of the STG tendon 212. The artificial ligaments 216 are prepared in the form of strings made of, for example, polyester or the like. A string 214*b* wound around the fixture 214*a* is used in taking the fixture 214*a* from the knee joint 100 to the outside of the femur 112 through a later-described concave hole 222 and a later-described through hole (a drilled hole) 220. An outer shape of a cross section of the STG tendon 212, which is perpendicular to a longitudinal axis, is an approximately rectangular shape, an approximately elliptical shape close to a rectangular shape, or the like. Furthermore, the outer shape of the STG tendon 212 has a size of, for example, about 4 mm×5 mm. It is preferable that, among the bone holes 220 and 222 and a bone hole 224 which will be described later, a position into which the STG tendon 212 is to be inserted has a size and a shape which conform to the outer shape of the STG tendon 212. Consequently, when the implanted tendon 210 is formed, a size of the STG tendon 212 is beforehand measured. It is to be noted that the STG tendon 212 is preferably collected before dissecting a region to which a damaged anterior cruciate ligament adheres.

It is preferable that the implanted tendon 210 is disposed in the same region as the region to which the damaged anterior cruciate ligament adheres. Because of this, the region to which the damaged anterior cruciate ligament adheres is dissected by using an unshown treatment unit, to clarify footprint regions 116 and 118 to which the anterior cruciate ligament has adhered. At this time, a suitable ultrasonic treatment instrument, an abrader, or the like are usable. Positions to form the later-described bone holes 220 and 224 to the footprint regions 116 and 118 are determined by marking or the like. A lateral cross section of the treatment portion 74 of the treatment instrument 52 mentioned above is not circular, thus the treatment portion has an orientation. Therefore, orientations of the bone holes 220 and 224 to be formed in the footprint regions 116 and 118 are also determined. Although not shown in the drawing, the footprint region 116 is present in a lateral wall posterior region of an intercondylar fossa of the femur 112. Furthermore, the footprint region 118 is present on an inner side of an anterior intercondylar area of the tibia 114.

Here, a procedure is performed using an inside-out method. To the femur 112, the drill (the first treatment unit) 30 is inserted from the suitable portal 104 into the joint cavity 110 of the knee joint 100. At this time, a distal end of the drill 30 can be brought directly into contact with the footprint region 116. Therefore, in a case where the bone hole 220 is formed, a known guide wire and a known guide are not required. Thus, a central area of a marked region of the footprint region 116 is cut from the inside of the joint 100 to the outside of the femur 112 with the drill 30, to form the through hole (the drilled hole) 220 shown in FIG. 8A straight to the femur 112. A diameter of the drill 30 is adjusted into such a diameter that the suspension fixture 214*a* (see FIG. 7) can be passed from a joint cavity 110 side through a cortical bone on an outer side of the femur 112. The drill 30 is pulled out from the portal 104 after the through hole 220 is formed.

Figure 8A:
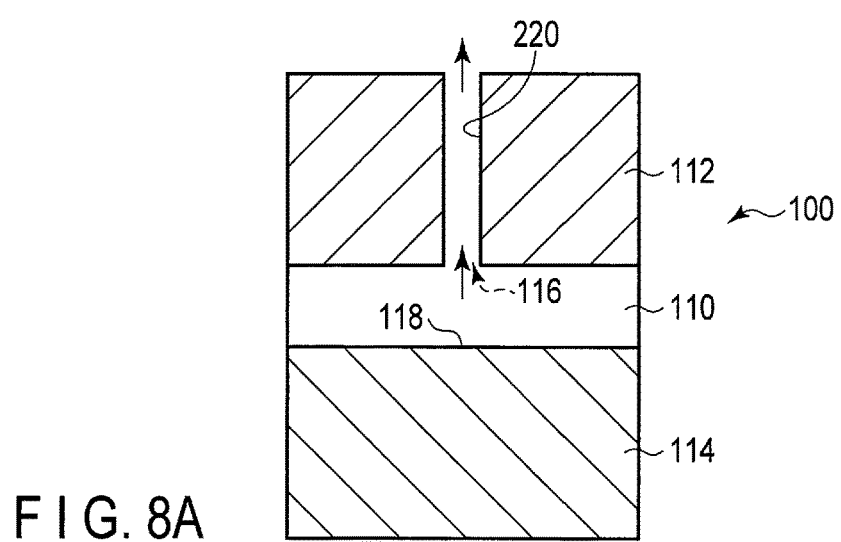
FIG. 8A is a schematic view showing a procedure of the reconstruction of the anterior cruciate ligament and showing a state where a through hole (a drilled hole) is formed from the inside of the knee joint to the footprint region of the anterior cruciate ligament of a femur of the knee joint with a drill.
Figure 8B:
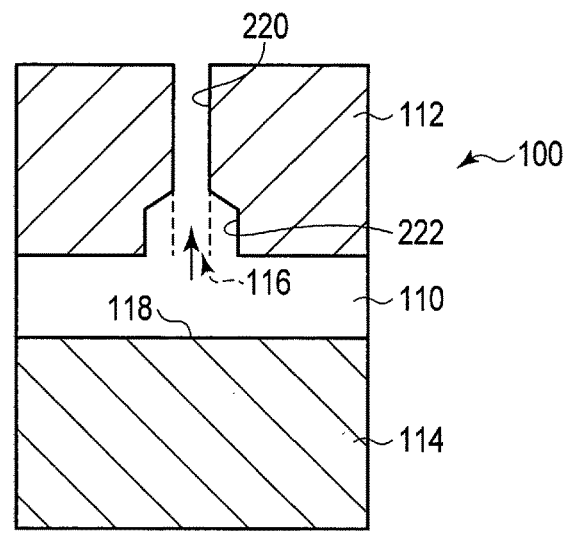
FIG. 8B is a schematic view showing a state where a concave hole is formed from the inside of the joint to the through hole of the femur in the state shown in FIG. 8A with the probe of the ultrasonic treatment instrument.

Next, as shown in FIG. 8B, the bone hole (the concave hole) 222 into which the implanted tendon 210 is inserted is formed by using the ultrasonic treatment instrument 52 shown in FIG. 2. After the implanted tendon 210 is prepared, the treatment portion 74 of the probe 66 of the ultrasonic treatment instrument 52 is attached to the opening edge of the bone hole 220 formed with the drill 30 in the joint 100. At this time, it is preferable that the vicinity of a distal end of the cutting portion 82 of the treatment instrument 52 which includes the top portion 86*c* of the convex portion 86*b* is present in the drilled hole 220.

A projection shape of the treatment portion 74 of the ultrasonic treatment instrument 52, when its proximal side is observed from the distal side along the longitudinal axis L, is formed in a size to cover the opening edge of the bone hole 220. Thus, the cross section of the pillar-shaped portion 86a of the treatment portion 74 of the ultrasonic treatment instrument 52 which is perpendicular to the longitudinal axis L has the same size and shape or about the same size and shape from the distal end 87a to the proximal end 87b. For this reason, in the state where the ultrasonic vibration is transmitted to the probe 66, the approximately rectangular parallelepiped concave hole (a second bone hole) 222 similar to the concave hole shown in FIG. 4B is formed in a predetermined orientation in the marked region of the footprint region 116 shown in FIG. 4B. That is, in the state where the ultrasonic vibration is transmitted to the treatment portion 74 of the ultrasonic treatment instrument 52, the ultrasonic vibration is applied from the treatment portion 74 to the femur 112. Consequently, the bone hole 220 of the femur 112 is cut from the inside of the knee joint 100 along a predetermined depth. As a result, a region of the bone hole 220 on a joint 100 side is expanded, thereby forming the bone hole 222 of a suitable shape to receive the implanted tendon 210. A bottom surface of the bone hole 222 is continuous with the bone hole 220.

At this time, the top portion 86c of the convex portion 86b of the cutting portion 82 of the treatment instrument 52 is inserted in the drilled hole 220, and hence during preparation of the concave hole 222, the drilled hole 220 can be a guide for the treatment instrument 52. Consequently, a central axis of the bone hole 222 matches or substantially matches a central axis of the bone hole 220 in the bottom surface of the bone hole 222. Therefore, the concave hole 222 is easily formed straight.

Figure 8C:
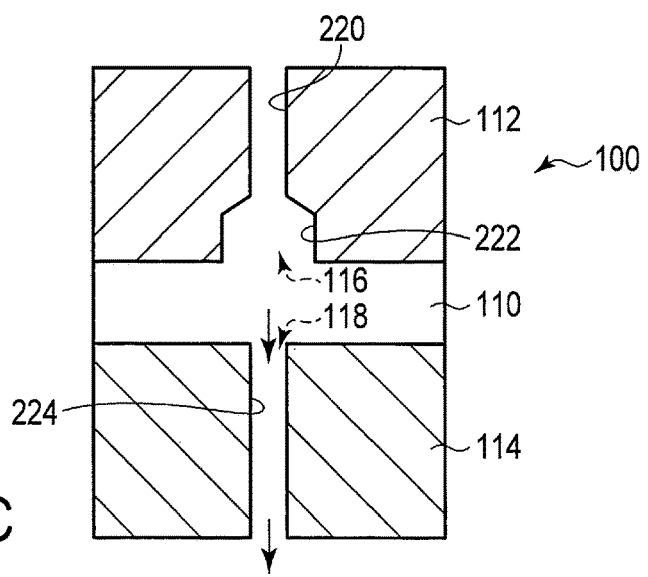
FIG. 8C is a schematic view showing a state where a through hole (a drilled hole) is formed from the inside of the knee joint to a footprint region of an anterior cruciate ligament of a tibia of the knee joint in the state shown in FIG. 8B with the drill.

Furthermore, also as to the tibia 114, a central area of a marked region of the footprint region 118 is cut from the inside of the joint 100 to the outside of the tibia 114 with the drill 30, to form the through hole (the drilled hole) 224 straight to the tibia 114 as shown in FIG. 8C. The through hole 224 may be formed to extend from the outside of the joint 100 through the footprint region 118 in the joint 100. Further, a concave hole 226 shown in FIG. 8D is formed in a predetermined orientation in the marked region of the footprint region 118 of the tibia 114 by use of the treatment instrument 52 to which the ultrasonic vibration is transmitted.

The fixture 214a at one end of the implanted tendon 210 by the STG tendon 212 is taken out from, for example, the second portal 104 to the outside of the femur 112 via the concave hole 222 and the drilled hole 220 of the femur 112. At this time, the outer shape of the STG tendon 212 is approximately rectangular as described above, thus the implanted tendon 210 is disposed in accordance with the orientation of the concave hole 222. On the other hand, the other end of the implanted tendon 210 is taken out from the tibia 114 via the concave hole 226 and the drilled hole 224 of the tibia 114. Then, a tensile force of the implanted tendon 210 is suitably adjusted in accordance with a bent state of the knee joint 100 to fix the other end of the implanted tendon 210 to the outer side of the tibia 114 with a fixture 218 such as a staple (a screw may be used) as shown in FIG. 8E.

To these approximately rectangular concave holes 222 and 226, the STG tendon 212 of the approximately rectangular implanted tendon 210 is disposed in accordance with the orientation of the concave holes 222 and 226. Thus, a clearance formed between the STG tendon 212 of the implanted tendon 210 and the concave hole 222 and a clearance formed between the STG tendon 212 and the concave hole 226 become smaller as much as possible. Furthermore, the clearance between the STG tendon 212 and the bone is small, and thus a space volume to be regenerated as the bone is smaller, facilitating the formation of a ligament by the STG tendon 212. Also, the clearance is decreased, whereby it is possible to decrease an amount of the joint liquid to enter the bone holes 222 and 226 and to inhibit enlargement of the bone holes 222 and 226 due to the joint liquid. Furthermore, the concave holes 222 and 226 are formed with the treatment portion 74 of the ultrasonic treatment instrument 52 having the block-shaped cutting portion 82 shown in FIG. 2, whereby the holes are not expanded with a dilator. Therefore, even in patients with low bone density, bone fracturing can be suppressed, so it is easy to perform an operation using the implanted tendon 210.

The shape of the concave holes 222 and 226 is copied from the shape of the treatment portion 74 of the probe 66 of the ultrasonic treatment instrument 52 shown in FIG. 2 and FIG. 3A. Because of this, in a case where the outer shape of the cross section of the pillar-shaped portion 86a of the treatment portion 74 of the probe 66 of the ultrasonic treatment instrument 52 which is perpendicular to the longitudinal axis L is not rectangular but is elliptical, the elliptical concave holes are formed. In a case where the outer shape of the cross section of the pillar-shaped portion 86a of the treatment portion 74 of the probe 66 of the ultrasonic treatment instrument 52, which is perpendicular to the longitudinal axis L, is not rectangular but is suitably polygonal, the concave holes of the polygonal shape are formed. The shape of the treatment portion 74 is selected in accordance with the shape of the STG tendon 212 of the implanted tendon 210.

It is to be noted that there has been described an example where the through hole 220 shown in FIG. 8A is formed by using the drill 30 here, but the through hole may be formed by applying the ultrasonic vibration from the treatment portion 74 to the femur 112 in a state where the ultrasonic vibration is transmitted to the treatment portion 74 of the ultrasonic treatment instrument 52. That is, it is also preferable that the suitable through hole 220 is formed with the ultrasonic treatment instrument 52.

The anterior cruciate ligament anatomically branches into two fiber bundles, so it is also preferable that two holes are made in each of the femur 112 and tibia 114, and that the implanted tendon 210 is passed through the respective holes.

According to the first procedure example, it can be considered as follows.

Each of an area of the footprint region 116 of the femur 112 of the anterior cruciate ligament and an area of the footprint region 118 of the tibia 114 is small. The outer shape of the STG tendon 212 of the implanted tendon 210 is different from a circular shape, and is a rectangular shape, an elliptical shape or the like. For example, when the STG tendon 212 with an outer shape of 5 mm×4 mm=20 mm$^2$ is to be inserted into a circular hole, a diameter of the circular hole needs to be about 6.5 mm. In a case where the circular hole is used in this way, about 40% of a region of the circular hole is a space other than a region in which the STG tendon 212 of the implanted tendon 210 is disposed. The joint liquid permeates this space, and the STG tendon 212 of the implanted tendon 210 may slowly form the ligament.

By suitably selecting the treatment portion 74 of the ultrasonic treatment instrument 52, the concave hole or the through hole having any shape such as the elliptical shape or the polygonal shape can be formed in a suitable depth. Therefore, when the concave holes 222 and 226 are suitably formed in accordance with the outer shape of the STG tendon 212 as shown in FIG. 8A to FIG. 8E, the space volume between the concave holes 222 and 226 and the STG tendon 212 can be smaller, and an amount of the femur 112 and the tibia 114 to be cut can be smaller. In the present embodiment, the ultrasonic probe 66 is suitably selected in accordance with the outer shape of the STG tendon 212, so that it is possible to suitably form the concave holes 222 and 226 while decreasing the amount of bone to be cut. Thus, the STG tendon 212 is fixed to the suitably formed concave holes 222 and 226, whereby the implanted tendon 210 can form the ligament sooner.

That is, the concave holes 222 and 226 can be formed by using the ultrasonic treatment instrument 52 including the treatment portion 74 having the pillar-shaped portion 86a of a rectangular, approximately rectangular, elliptical or approximately elliptical cross section. Therefore, it is possible to form the concave holes 222 and 226 having the same outer shape or approximately the same outer shape as the outer shape of the STG tendon 212 of the implanted tendon 210, and it is possible to appropriately bury and fix the STG tendon 212 into the concave holes 222 and 226.

Also, in a case where the concave hole 222 is formed with the treatment portion 74 of the ultrasonic treatment instrument 52, it is possible to perform a treatment of forming the concave hole 222 in a state where a part of a distal end of the treatment portion 74 is fitted into the previously formed through hole 220. As a result, in a case of using this procedure, it is easy to match the central axis of the previously formed through hole 220 with the central axis of the concave hole 222 to be formed later. Furthermore, when the ultrasonic treatment instrument 52 is used, it is easier to form the concave hole or the through hole at a desired position as compared with a case where the drill is used. Therefore, in the desired regions of the footprint regions 116 and 118 of the anterior cruciate ligament, it is possible to form the bone holes 222 and 226 in which the STG tendon 212 of the implanted tendon 210 is disposed without projecting, to the greatest extent possible, in a desired orientation. Because of this, in the femur 112, invasion into a peripheral tissue of the footprint regions 116 and 118 of the anterior cruciate ligament is prevented.

As described above, the lateral cross section of the implanted tendon 210 varies in vertical×horizontal lengths. In a case where the ultrasonic treatment instrument 52 shown in FIG. 2 is used, a cross section of each of the concave holes 222 and 226 is, for example, rectangular. For this reason, when the concave holes 222 and 226 are formed in the appropriate orientation, it is easy to optimize the orientation in a state where the STG tendon 212 of the implanted tendon 210 is implanted.

In this procedure, the example has been described where the suitable regions of the footprint regions 116 and 118 are marked, but the marking is not necessarily required.

A second procedure example will be described with reference to FIG. 9 and FIG. 10A to FIG. 10G. FIG. 10A to FIG. 10G schematically show a state where the femur 112, the tibia 114 and the joint cavity 110 of the knee joint 100 are seen from the anterior side. Arrows in FIG. 10A to FIG. 10F indicate a bone excising direction.

Here, the example is described where a patellar tendon 232 to which bone fragments 232a and 232b adhere at both ends is used as an implanted tendon 230. One bone fragment 232a is a part of a patella (not shown). The bone fragment 232a on a patella side has an approximately triangular pillar shape. The other bone fragment 232b is a part of the tibia 114. The bone fragment 232b on a tibia 114 side is rectangular parallelepiped. An outer shape of each of the bone fragments 232a and 232b has a size of, for example, about 10 mm×5 mm. Such an implanted tendon is referred to as the BTB tendon.

Figure 9:
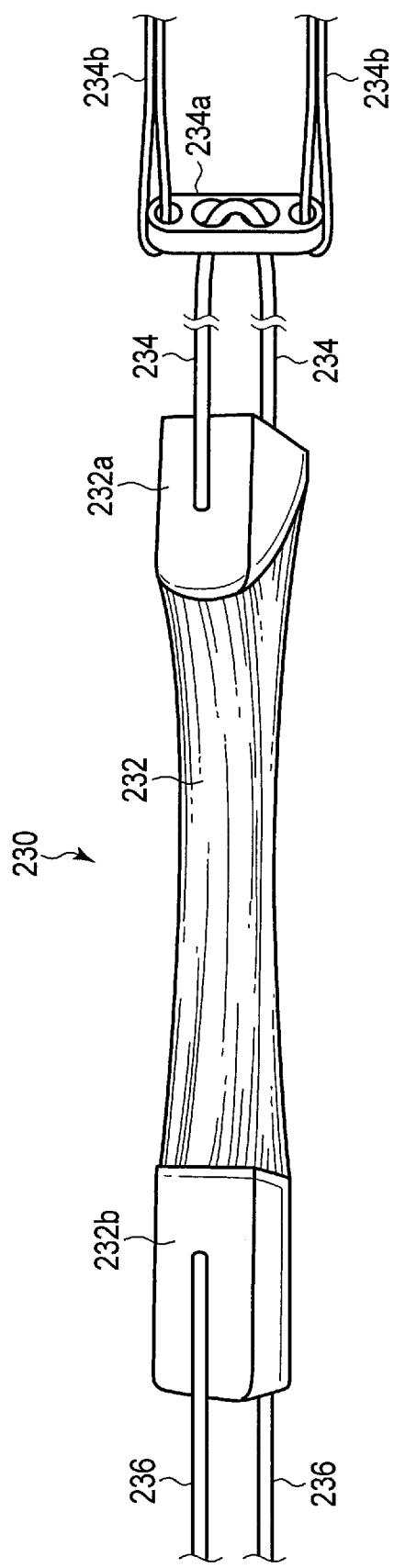
FIG. 9 is a schematic view of an implanted tendon which includes a BTB tendon for use in the reconstruction of the anterior cruciate ligament.

As shown in FIG. 9, the implanted tendon 230 has the BTB tendon 232, a suspension fixture 234a disposed in the bone fragment 232a at one end of the BTB tendon 232 via a suture thread 234 and, for example, a pair of suture threads 236 fixed to the bone fragment 232b at the other end of the BTB tendon 232. It is to be noted that a suture thread 234b wound around the fixture 234a is used in taking the fixture 234a from the knee joint 100 to the outside of the femur 112 through later-described concave holes 242a and 242b and a later-described through hole 240.

It is preferable that the later-described bone holes 242a and 242b, into which the bone fragment 232a of the BTB tendon 232 is inserted, and later-described bone holes 246a and 246b, into which the bone fragment 232b is inserted, have sizes and shapes which conform to an outer shape of the BTB tendon 232, respectively.

It is preferable that the BTB tendon 232 is collected before dissecting a region to which the damaged anterior cruciate ligament adheres. Thus, a size of the outer shape of each of the bone fragments 232a and 232b is beforehand measured.

Here, a procedure is performed using the inside-out method. Descriptions of those parts that are the same as in the procedure of the STG tendon 212 are omitted whenever possible.

With the drill 30, the through hole (a drilled hole) 240 shown in FIG. 10A is formed straight to the femur 112 through the footprint region 116 of the femur 112. That is, the bone hole 240 is cut and formed from the inside of the joint 100 toward the outside of the femur 112. To the femur 112, the drill (the first treatment unit) 30 is inserted from the suitable portal 104 into the joint cavity 110 of the knee joint 100. Further, a diameter of the drill 30 is adjusted into such a diameter that the suspension fixture 234a can be passed from the joint cavity 110 side through a cortical bone on the outer side of the femur. The drill 30 is pulled out from the portal 104 after the through hole 240 is formed.

Next, the treatment portion 74 of the ultrasonic treatment instrument 52 is attached to a position that shifts from the opening edge of the bone hole 240 formed with the drill 30 in the joint 100. At this time, the vicinity of the distal end of the cutting portion 82 of the treatment instrument 52 which includes the top portion 86c of the convex portion 86b may be present on an inner or outer side of the drilled hole 240. As shown in FIG. 10B, the concave hole 242a into which the implanted tendon 230 is to be inserted is formed by using the ultrasonic treatment instrument 52 shown in FIG. 2.

The projection shape of the treatment portion 74 of the ultrasonic treatment instrument 52 when its proximal side is observed from the distal side along the longitudinal axis L is approximately rectangular. Further, the cross section of the pillar-shaped portion 86a of the treatment portion 74 of the ultrasonic treatment instrument 52 which is perpendicular to the longitudinal axis L has the same size and shape or about the same size and shape from the distal end 87a to the proximal end 87b. Consequently, in the state where the ultrasonic vibration is transmitted to the probe 66, the approximately rectangular parallelepiped first concave hole (a second bone hole) 242a shown in FIG. 10B is formed similarly to the concave hole shown in FIG. 4B. At this time, the first concave hole 242a is formed straight.

Further, the second concave hole 242b shown in FIG. 10C is formed adjacent to the first concave hole 242a with the same treatment portion 74 of the ultrasonic treatment instrument 52. At this time, the treatment is performed while the treatment portion 74 of the ultrasonic treatment instrument 52 is left in the joint 100. The first concave hole 242a must be in communication with the second concave hole 242b. Therefore, when necessary, a bone tissue between the first concave hole 242a and the second concave hole 242b is removed by cutting. In this way, a bone hole of an outer shape required for the concave holes 242a and 242b is formed into a desired size and a desired shape by pressing the treatment portion 74 of the ultrasonic treatment instrument 52 at a position adjacent to the bone hole 242a once or a number of times. Therefore, an outer shape of 4 mm×5 mm of one concave hole 242a is continuous with an outer shape of 4 mm×5 mm of another concave hole 242b, additionally, the treatment is suitably performed with the treatment portion 74 of the ultrasonic treatment instrument 52. Because of this, the concave holes 242a and 242b cooperate to form one bone hole (the second bone hole) of an outer shape of 10 mm×5 mm into which the bone fragment 232a is insertable.

Also as to the tibia 114, a through hole 244 shown in FIG. 10D is formed from the inside of the joint 100 to the outside of the tibia 114 in the footprint region 118 on the tibia 114 side with the drill 30.

As shown in FIG. 10E, the concave hole 246a is formed in the footprint region 118 of the tibia 114 by the ultrasonic vibration.

Figure 10F:
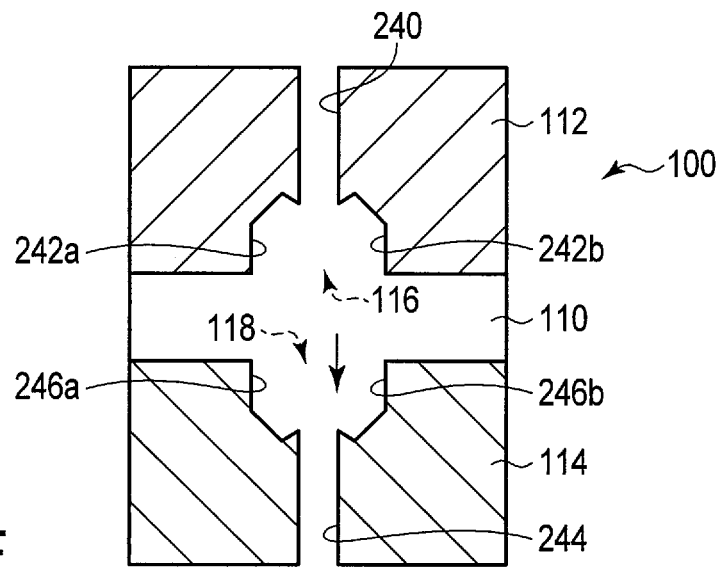
FIG. 10F is a schematic view showing a state where a concave hole is formed from the inside of the joint at a position that is adjacent to the concave hole of the tibia in the state shown in FIG. 10E and that includes the through hole of the tibia with the probe of the ultrasonic treatment instrument.
Figure 10G:
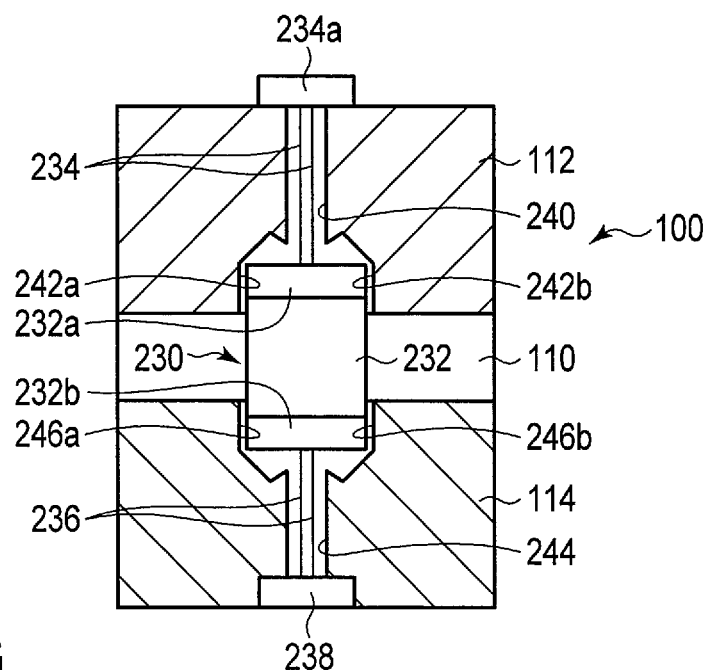
FIG. 10G is a schematic view showing a state where the implanted tendon including the BTB tendon shown in FIG. 9 is fixed to the femur and the tibia.

As shown in FIG. 10F, the concave hole 246b that is continuous with the concave hole 246a is formed in the footprint region 118 of the tibia 114. A bone hole of an outer shape required for the concave holes 246a and 246b is formed into a desired size and a desired shape by pressing the treatment portion 74 of the ultrasonic treatment instrument 52 at a position adjacent to the bone hole 246a once or a number of times. Therefore, an outer shape of 4 mm×5 mm of one concave hole 246a is continuous with an outer shape of 4 mm×5 mm of another concave hole 246b, and further, the treatment is suitably performed with the treatment portion 74 of the ultrasonic treatment instrument 52. Consequently, the concave holes 246a and 246b cooperate to form one bone hole of an outer shape of 10 mm×5 mm into which the bone fragment 232b can be inserted.

Further, one bone fragment 232a of the implanted tendon 230 by the BTB tendon 232 is inserted from, for example, the second portal 104 into the concave holes 242a and 242b of the femur 112. At this time, the fixture 234a is taken out from the femur 112 via the drilled hole 240. The one bone fragment 232a of the implanted tendon 230 is disposed in accordance with an orientation of the concave holes 242a and 242b. It is to be noted that as described above, an outer shape of the one bone fragment 232a of the implanted tendon 230 is a triangular pillar shape.

The other bone fragment 232b of the implanted tendon 230 is disposed in the concave holes 246a and 246b of the tibia 114 to take the suture threads 236 attached to the bone fragment 232b to the outside of the tibia 114 via the drilled hole 244. Further, a tensile force of the implanted tendon 230 is suitably adjusted in accordance with the bent state of the knee joint 100 to fix the suture threads 236 of the implanted tendon 230 to the outer side of the tibia 114 with a fixture 238 such as a staple (a screw may be used) (see FIG. 10G).

According to the second procedure example, it can be considered as follows.

The outer shape of each of the bone fragments 232a and 232b at the ends of the BTB tendon 232 of the implanted tendon 230 is different from a circular shape and is a rectangular parallelepiped shape or an approximately triangular pillar shape. For example, when the BTB tendon 232 of 5 mm×10 mm=50 mm$^2$ is to be inserted into the circular hole, a diameter of the circular hole needs to be about 11 mm. In this case, a cross-sectional area of the circular hole is about 95 mm$^2$ and about a half becomes a space. The joint liquid permeates this space and formation of a ligament by the BTB tendon 232 of the implanted tendon 230 might become slow.

Consequently, when the concave holes 242a, 242b, 246a and 246b are suitably formed in accordance with the outer shape of the bone fragments 232a and 232b of the BTB tendon 232 as shown in FIG. 10A to FIG. 10G, it is possible to decrease each of a space volume between the concave holes 242a and 242b and the bone fragment 232a of the BTB tendon 232 and a space volume between the concave holes 246a and 246b and the bone fragment 232b of the BTB tendon 232, and it is possible to decrease an amount of the femur 112 and the tibia 114 that is cut. In the present embodiment, the ultrasonic probe 66 is suitably selected in accordance with the outer shape of the bone fragments 232a and 232b of the BTB tendon 232, so that it is possible to suitably form the concave holes 242a, 242b, 246a and 246b while decreasing the amount of cut bone. Further, the bone fragments 232a and 232b are fixed to the suitably formed concave holes 242a, 242b, 246a and 246b, whereby it is possible to more quickly form the ligament by the implanted tendon 230.

That is, it is possible to form the concave holes 242a, 242b, 246a and 246b by use of the ultrasonic treatment instrument 52 including the treatment portion 74 having the pillar-shaped portion 86a of the rectangular, approximately rectangular, elliptical or approximately elliptical cross section. Consequently, it is possible to form the concave holes 242a, 242b, 246a and 246b having the same outer shape or about the same outer shape as the outer shape of the bone fragments 232a and 232b of the BTB tendon 232 of the implanted tendon 230, and it is possible to appropriately bury and fix the bone fragments 232a and 232b into the concave holes 242a, 242b, 246a and 246b.

Further, when the ultrasonic treatment instrument 52 is used, it is easier to form a position to form the concave hole or the through hole at a desired position as compared with a case where the drill is used. Consequently, it is possible to form the bone holes 242a, 242b, 246a and 246b in which the end portions of the implanted tendon 230 are disposed without projecting as much as possible, to the footprint regions 116 and 118 of the anterior cruciate ligament. Consequently, in the femur 112, there is prevented invasion into a peripheral tissue of the footprint region 116 of the anterior cruciate ligament.

Furthermore, as described above, the lateral cross section of the implanted tendon 230 varies in vertical×horizontal lengths. In a case where the ultrasonic treatment instrument 52 shown in FIG. 2 is used, the cross section of each concave hole is, for example, rectangular. Consequently, when the concave holes are formed in the appropriate orientation, it is easy to optimize the orientation in a state where the BTB tendon 232 of the implanted tendon 230 is implanted.

There will be described another procedure example where the implanted tendon 230 having the BTB tendon 232 is used with reference to FIG. 11A to FIG. 11D. Arrows in FIG. 11A to FIG. 11C indicate a bone excising direction.

Figure 11A:
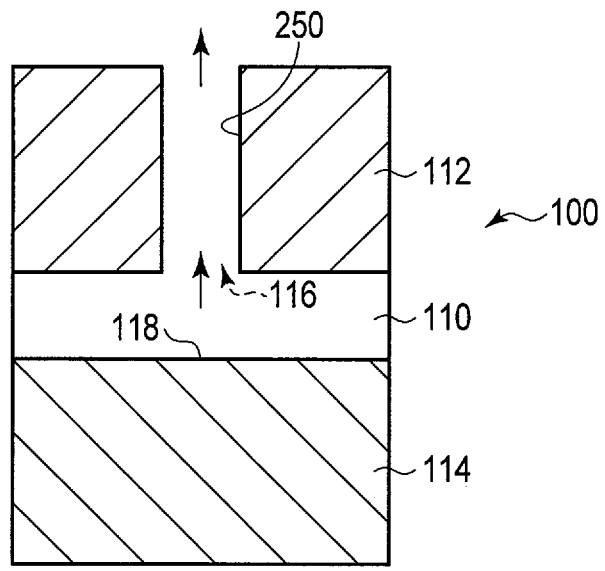
FIG. 11A is a schematic view showing a procedure of the reconstruction of the anterior cruciate ligament and showing a state where a through hole (a drilled hole) is formed from the inside of the knee joint to the footprint region of the anterior cruciate ligament of the femur of the knee joint with the drill.

A drilled hole 250 shown in FIG. 11A is formed from the footprint region 116 of the femur 112 to the outside of the femur 112.

Figure 11B:
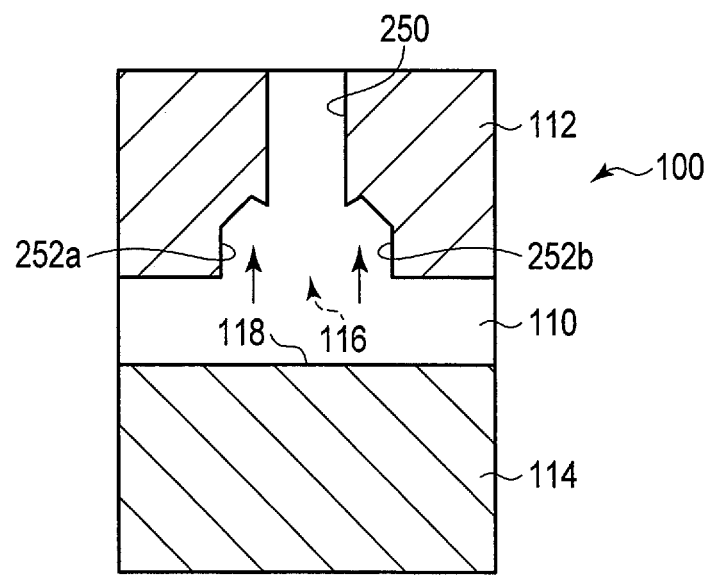
FIG. 11B is a schematic view showing a state where concave holes are formed from the inside of the joint at a position including, in a middle, the through hole of the femur in the state shown in FIG. 11A with the probe of the ultrasonic treatment instrument.

In the state where the ultrasonic vibration is transmitted to the treatment portion 74 of the ultrasonic treatment instrument 52 shown in FIG. 2, concave holes 252a and 252b which communicate with the drilled hole 250 as shown in FIG. 11B are formed from the inside of the joint cavity 110 toward the outside of the femur 112.

Figure 11C:
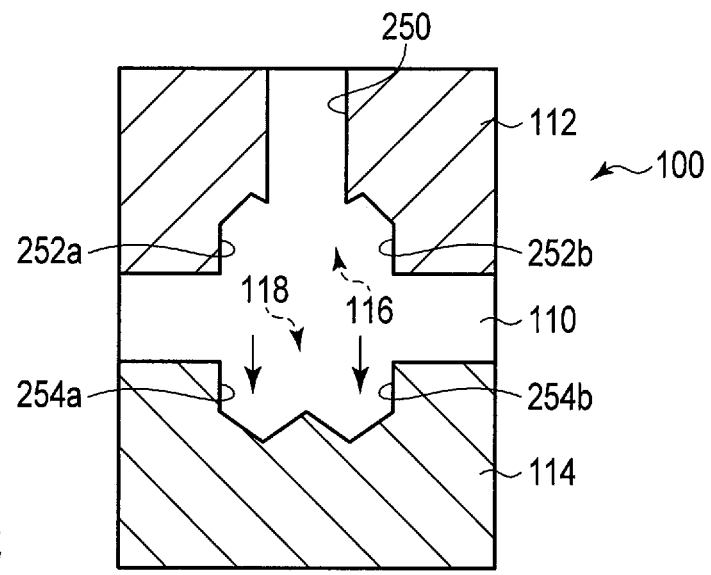
FIG. 11C is a schematic view showing a state where concave holes are formed from the inside of the knee joint to the footprint region of the anterior cruciate ligament of the tibia of the knee joint shown in FIG. 11B with the probe of the ultrasonic treatment instrument.
Figure 11D:
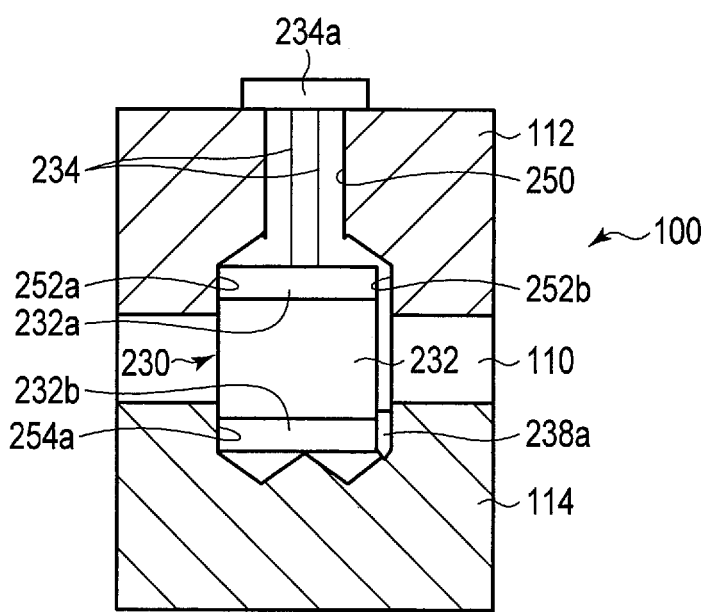
FIG. 11D is a schematic view showing a state where the implanted tendon including the BTB tendon shown in FIG. 9 is fixed to the tibia with screws.

Concave holes 254a and 254b shown in FIG. 11C are formed from the inside of the joint cavity 110 toward the outside of the tibia 114 in the footprint region 118 of the tibia 114 while the treatment portion 74 of the ultrasonic treatment instrument 52 shown in FIG. 2 is left in the joint cavity 110 as it is.

For example, one bone fragment 232a of the BTB tendon 232 is inserted tom the second portal 104 into the concave holes 252a and 252b of the femur 112. At this time, the fixture 234a is taken out from the femur 112 via the drilled hole 250. On the other hand, the other bone fragment 232b of the BTB tendon 232 is disposed in the concave holes 254a and 254b of the tibia 114 to fix the bone fragment 232b to the concave holes 254a and 254b with a screw 238a (see FIG. 11D).

A third procedure example will be described with reference to FIG. 12A to FIG. 12F. FIG. 12A to FIG. 12F schematically show a state where the femur 112, the tibia 114 and the joint cavity 110 of the knee joint 100 are seen from the anterior side. Arrows in FIG. 12A to FIG. 12E indicate a bone excising direction. Here, a case of using an STG tendon is described.

Figure 12A:
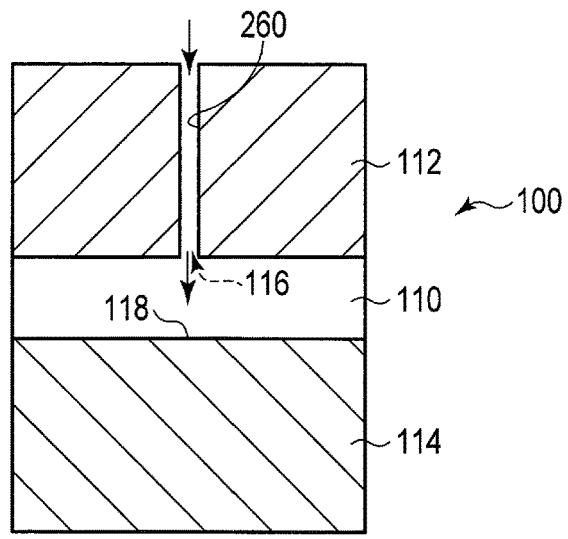
FIG. 12A is a schematic view showing a procedure of the reconstruction of the anterior cruciate ligament and showing a state where a through hole is formed from the outside of the femur toward the footprint region of the anterior cruciate ligament of the femur of the knee joint.

A guide wire (e.g., a diameter of 2.5 mm) for the drill is inserted from the outside of the femur 112 toward the footprint region 116 of the femur 112 by use of an unshown known guide. That is, by an outside-in method, a bone hole 260 shown in FIG. 12A is formed from the outside of the femur 112 toward the inside of the joint 100. At this time, it is preferable to pass the guide wire through the footprint region 116 of the femur 112.

Figure 12B:
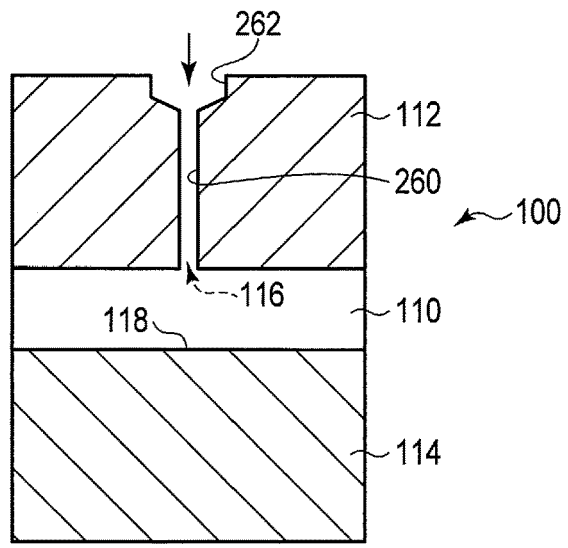
FIG. 12B is a schematic view showing a state where a cortical bone on an outer side of the femur is removed with the drill to the through hole of the femur in the state shown in FIG. 12A.

The drill 30 guided along the guide wire is passed through the cortical bone on a surface side in the vicinity of the outside of the femur 112, to form a concave hole 262 shown in FIG. 12B. The concave hole 262 is circular. Further, the drill 30 and the guide wire are removed. At this time, the through hole 260 having the diameter of 2.5 mm is formed by the guide wire.

Figure 12C:
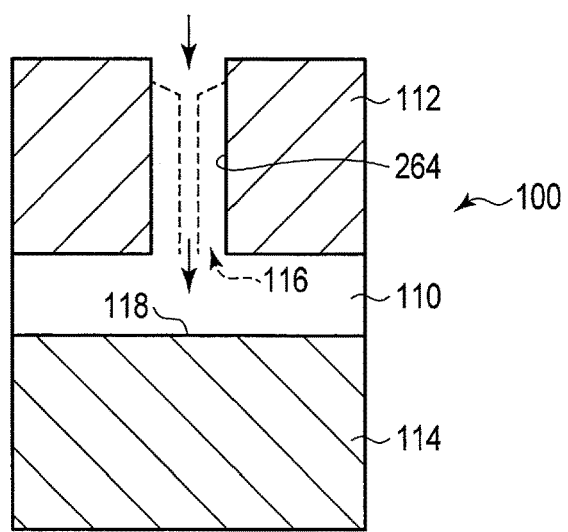
FIG. 12C is a schematic view showing a state where a through hole is formed from the outside of the femur of the knee joint in the state shown in FIG. 12B to the footprint region of the anterior cruciate ligament with the ultrasonic treatment instrument.

A through hole 264 shown in FIG. 12C is formed from the outside of the femur 112 toward the knee joint 100 side by use of the ultrasonic treatment instrument 52 including the treatment portion 74 having, for example, the shape shown in FIG. 2. The through hole 264 has the same rectangular cross section or about the same rectangular cross section as the outer shape of the STG tendon 212 of the implanted tendon 210.

It is also preferable that the through hole 264 is formed with the treatment portion 74 of one of FIG. 5A to FIG. 6C. The cortical bone of an outer surface of the femur 112 is very hard, and hence there is the fear that much time is taken in cutting the bone with the ultrasonic treatment instrument 52. On the other hand, the cortical bone is already removed by the concave hole 262 formed with the drill 30. Consequently, it is easy to cut a cancellous bone with the ultrasonic treatment instrument 52.

It is to be noted that, for example, the treatment portion 74 of the ultrasonic treatment instrument 52 is strengthened to increase an amplitude of the treatment portion 74, whereby in place of the cutting of the cortical bone with the drill 30, both the cutting of the cortical bone and the cutting of the cancellous bone can be performed once with the ultrasonic treatment instrument 52.

Figure 12D:
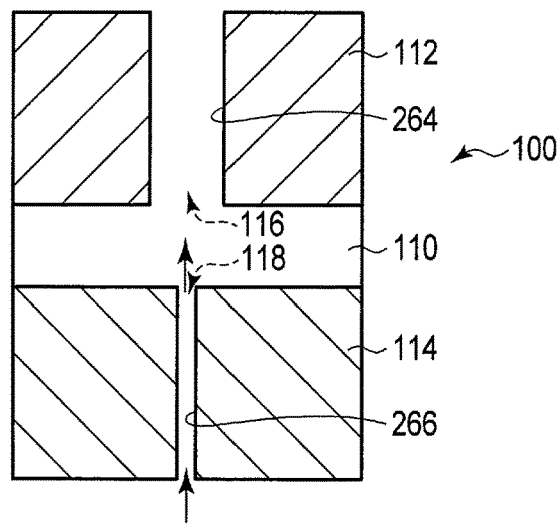
FIG. 12D is a schematic view showing a state where a through hole is formed from the outside of the tibia toward the footprint region of the anterior cruciate ligament of the tibia of the knee joint.
Figure 12E:
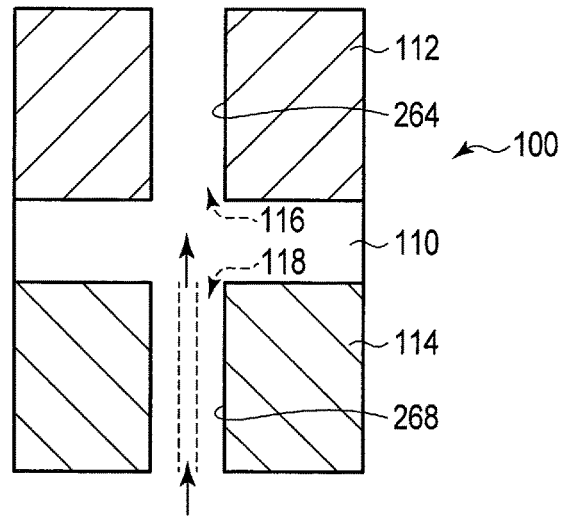
FIG. 12E is a schematic view showing a state where a through hole is formed from the outside of the tibia of the knee joint in the state shown in FIG. 12D to the footprint region of the anterior cruciate ligament with the ultrasonic treatment instrument.
Figure 12F:
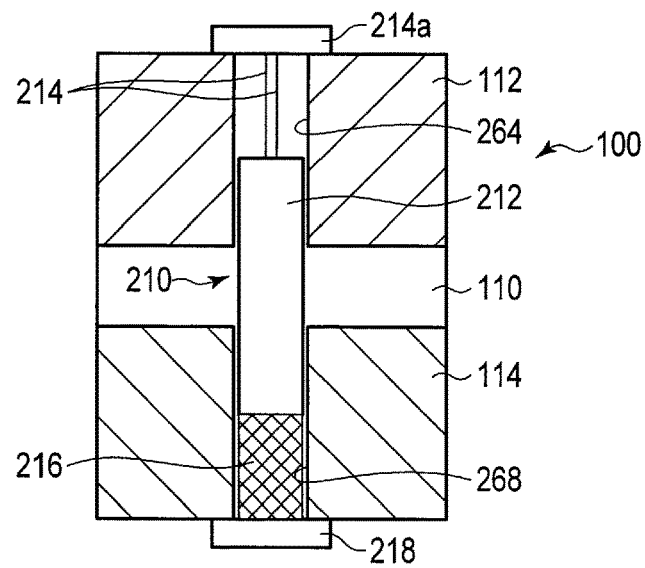
FIG. 12F is a schematic view showing a state where the implanted tendon including the STG tendon shown in FIG. 7 is fixed to the femur and the tibia.

The guide wire (e.g., the diameter of 2.5 mm) for the drill is inserted from the outside of the tibia 114 toward the footprint region 118 of the tibia 114 by use of the known guide, to form a through hole 266 shown in FIG. 12D. With the drill 30 guided from the outside of the tibia 114 toward the footprint region 118 of the tibia 114 along the guide wire, a through hole 268 extending from the outside of the tibia 114 through the footprint region 118 of the tibia 114 is formed as shown in FIG. 12E. The through hole 268 is circular. It is to be noted that the rectangular through hole 268 is preferably formed with the treatment instrument 52 shown in FIG. 2 in place of the drill 30.

Further, for example, the string 214b wound around the fixture 214a is taken out from the femur 112 through the through hole 268 of the tibia 114 and the through hole 264 of the femur 112, and the fixture 214a is taken out from the femur 112. At this time, as described above, the outer shape of the STG tendon 212 is approximately rectangular, and hence the STG tendon 212 is disposed in the femur 112 in accordance with an orientation of the through hole 264. Further, when necessary, the string 214b is cut or removed from the fixture 214a.

On the other hand, the artificial ligaments 216 at the other end of the implanted tendon 210 is held on the outer side of the tibia 114. Further, the tensile force of the implanted tendon 210 is suitably adjusted in accordance with the bent state of the knee joint 100 to fix the artificial ligaments 216 of the implanted tendon 210 to the outer side of the tibia 114 with the fixture 218, e.g., a staple or the like.

Depending on the patient, there might be a case where the patient cannot take a deeply bent body position. Even in such a case, the bone hole 264 can be formed to the femur 112 in this manner by the outside-in method.

It is to be noted that there has been described the case where the STG tendon 212 shown in FIG. 7 is used as the implanted tendon here, but the BTB tendon 232 (see FIG. 9) is also usable as the implanted tendon.

A fourth procedure example will be described with reference to FIG. 13A to FIG. 13E. FIG. 13A to FIG. 13E schematically show a state where the femur 112, the tibia 114 and the joint cavity 110 of the knee joint 100 are seen from the anterior side. Arrows in FIG. 13A to FIG. 13D indicate a bone excising direction.

Here, there is simply described a transtibial method of forming a bone hole (a concave hole) 278 in the femur 112 via a bone hole 276 formed in the tibia 114.

Figure 13A:
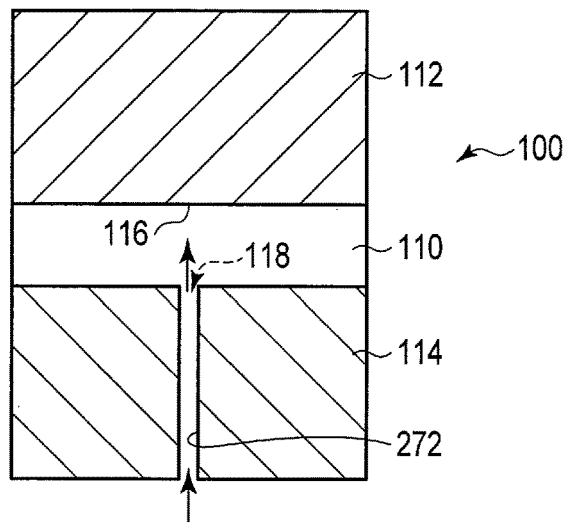
FIG. 13A is a schematic view showing a procedure of the reconstruction of the anterior cruciate ligament and showing a state where a through hole is formed from the outside of the tibia toward the footprint region of the anterior cruciate ligament of the tibia of the knee joint.
Figure 13B:
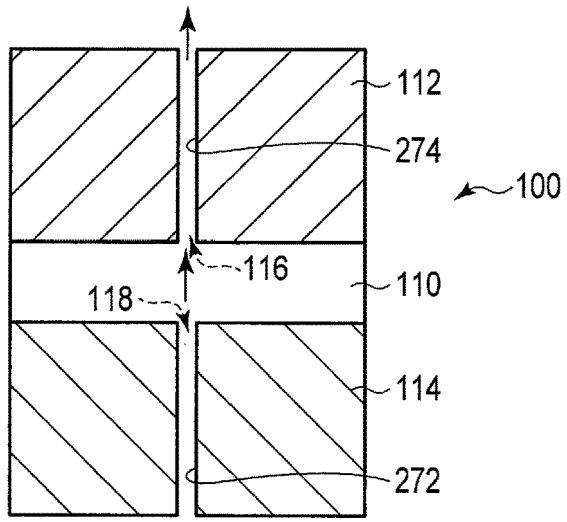
FIG. 13B is a schematic view showing a state where a through hole is formed in an outer side of the femur continuously with the through hole of the tibia in the state shown in FIG. 13A through the footprint region of the anterior cruciate ligament of the femur.

The guide wire for the drill is inserted from the outside of the tibia 114 toward the footprint region 118 of the tibia 114 by use of the known guide. As shown in FIG. 13A, a wire hole 272 is formed. Furthermore, a through hole (a concave hole may be formed) 274 is formed from the footprint region 118 of the tibia 114 through the footprint region 116 of the femur 112 toward the outside of the femur 112 with the guide wire for the drill as shown in FIG. 13B. Afterward, the guide wire is removed.

Figure 13C:
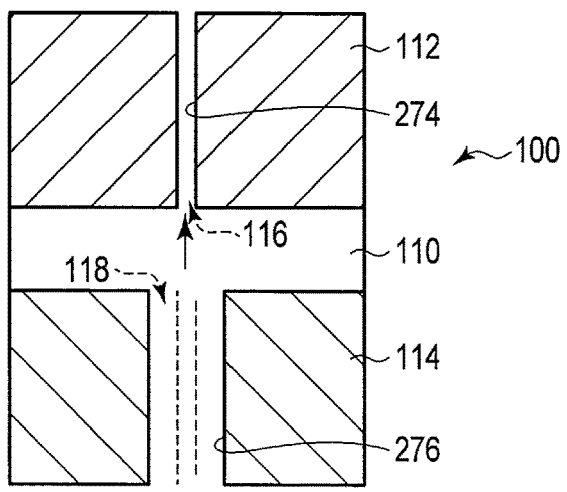
FIG. 13C is a schematic view showing a state where a through hole is formed from the outside of the tibia of the knee joint in the state shown in FIG. 13B to the footprint region of the anterior cruciate ligament with the ultrasonic treatment instrument.

In a state where the ultrasonic vibration is generated in the transducer 56b of the ultrasonic treatment instrument 52, the treatment portion 74 is pushed from the outside of the tibia 114 toward the footprint region along the guide hole 272 of the tibia 114. Consequently, the through hole 276 shown in FIG. 13C is formed.

Figure 13D:
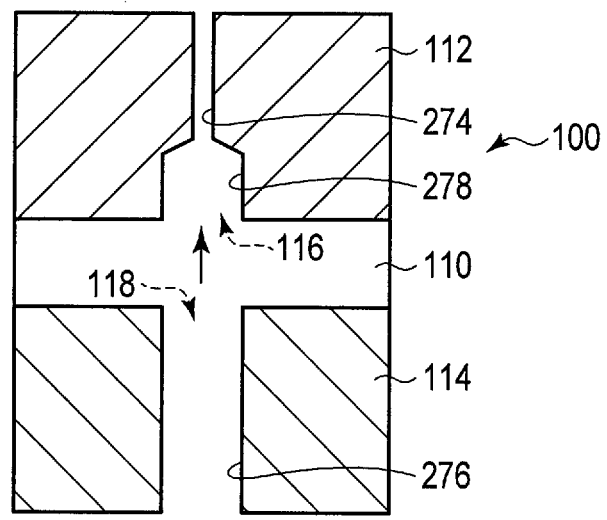
FIG. 13D is a schematic view showing a state where a concave hole is formed continuously with the through hole of the tibia in the state shown in FIG. 13C to the footprint region of the anterior cruciate ligament of the femur of the knee joint.
Figure 13E:
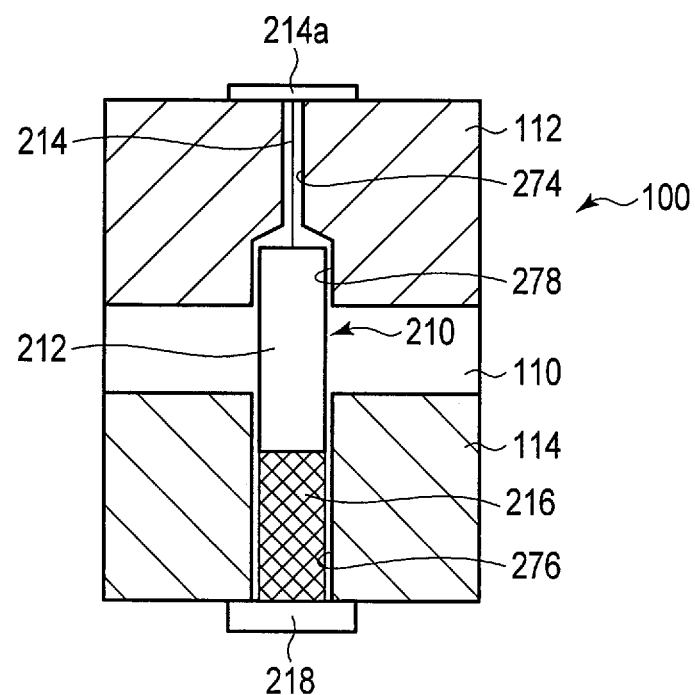
FIG. 13E is a schematic view showing a state where the implanted tendon including the STG tendon shown in FIG. 7 is fixed to the femur and the tibia.

Furthermore, a bone hole 278 shown in FIG. 13D is formed from the footprint region 118 of the tibia 114 toward the outside of the femur 112 through the footprint region 116 of the femur 112 along the guide hole 274 with the treatment portion 74 of the ultrasonic treatment instrument 52. The bone hole 278 has an approximately rectangular cross section.

Further, the fixture 214a at one end of the implanted tendon 210 by the STG tendon 212 is taken out from the femur 112 through, for example, the knee joint 100 from the outside of the tibia 114. At this time, the outer shape of the STG tendon 212 is approximately rectangular as described above, and hence the STG tendon 212 is disposed in accordance with an orientation of the concave hole 278. On the other hand, the other end of the STG tendon 212 maintains a state where the end is disposed on the outer side of the tibia 114. Further, the tensile force of the implanted tendon 210 is suitably adjusted in accordance with the bent state of the knee joint 100 to fix the other end of the implanted tendon 210 to the outer side of the tibia 114 with the fixture 218, e.g., the staple or the like (see FIG. 13E).

The bone hole 278 is formed in the femur 112 through the tibia 114, and hence the bone hole 278 can be formed without deeply bending the knee joint 100. Furthermore, the guide wire and the treatment portion 74 of the ultrasonic treatment instrument 52 can directly abut on the footprint region 116 of the anterior cruciate ligament in the femur 112, and hence it is possible to securely form the bone hole in the footprint region 116 of the femur 112.

Hitherto, the examples of the procedure of reconstructing the anterior cruciate ligament have been described, but it is possible to similarly perform the procedure on a posterior cruciate ligament, thereby reconstructing the ligament.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical procedure of preparing bone holes to attach an implanted tendon to a target bone when performing reconstruction of a ligament, comprising:
    forming a first bone hole in the target bone with a drill that digs the first bone hole in the target bone by rotation; and
    forming a second bone hole in the target bone with an ultrasonic treatment instrument that shatters the bone by ultrasonic vibration, the second bone hole being configured for insertion of the implanted tendon, wherein:
    the second bone hole is formed by laterally repositioning the ultrasonic treatment instrument to form a plurality of adjoining bone holes with the ultrasonic treatment instrument in the bone; and
    the second bone hole, when formed, has a bottom surface including the first bone hole.

2. The surgical procedure according to claim 1, wherein the forming the first bone hole includes inserting the drill into a knee joint through a portal of a knee,
    the forming the second bone hole includes inserting the ultrasonic treatment instrument into the knee joint through the portal of the knee, and
    the target bone is a femur.

3. The surgical procedure according to claim 2, wherein the forming the first bone hole includes forming by driving the drill to abut on the femur from an inside to an outside of the knee joint.

4. The surgical procedure according to claim 2, wherein the forming the second bone hole includes forming by driving the ultrasonic treatment instrument to abut on the femur from an inside to an outside of the knee joint.

5. The surgical procedure according to claim 1, wherein the first bone hole is a through hole.

6. The surgical procedure according to claim 1, wherein the forming the second bone hole includes forming the second bone hole to have a polygonal shape or an elliptical shape suitable for the implanted tendon.

7. The surgical procedure according to claim 1, wherein the forming the first bone hole includes forming the first bone hole to have a cylindrical shape.

8. The surgical procedure according to claim 1, wherein the forming the second bone hole includes:
    forming a first-second bone hole; and
    forming a second-second bone hole.

9. The surgical procedure according to claim 8, wherein the forming the second-second bone hole includes abutting the ultrasonic treatment instrument on a position adjacent to first-second bone hole, and shattering the bone by the ultrasonic vibration.

10. The surgical procedure according to claim 8, wherein the forming the first-second bone hole includes shallowing the first-second bone hole with respect to the first bone hole.

11. The surgical procedure according to claim 9, wherein the forming the second-second bone hole includes shallowing the second-second bone hole with respect to the first bone hole.

12. The surgical procedure according to claim 8, wherein the forming the first-second bone hole includes abutting the ultrasonic treatment instrument so that a center of the first-second bone hole differs from a center of the first bone hole, and shattering the bone by the ultrasonic vibration.

13. The surgical procedure according to claim 12, wherein the forming the second-second bone hole includes abutting the ultrasonic treatment instrument so that a center of the second-second bone hole differs from a center of the first bone hole, and shattering the bone by the ultrasonic vibration.

14. The surgical procedure according to claim 8, wherein the forming the first-second bone hole includes abutting the ultrasonic treatment instrument to include at least a part of the first bone hole, and shattering the bone by the ultrasonic vibration.

15. The surgical procedure according to claim 14, wherein the forming the second-second bone hole includes abutting the ultrasonic treatment instrument to include at least a part of the first bone hole, and shattering the bone by the ultrasonic vibration.

16. The surgical procedure according to claim 1, wherein the plurality of adjoining bone holes are formed by withdrawing the ultrasonic treatment instrument from the second bone hole after a previous one of the adjoining holes is formed and cutting an additional one of the plurality of adjoining bone holes by commencing the cutting at an exterior surface of the target bone.

* * * * *